(12) United States Patent
Ehrich

(10) Patent No.: US 8,206,927 B2
(45) Date of Patent: Jun. 26, 2012

(54) METHOD FOR ACCURATE ASSESSMENT OF DNA QUALITY AFTER BISULFITE TREATMENT

(75) Inventor: Mathias Ehrich, San Diego, CA (US)

(73) Assignee: Sequenom, Inc., San Diego, CA (US)

( * ) Notice: Subject to any disclaimer, the term of this patent is extended or adjusted under 35 U.S.C. 154(b) by 372 days.

(21) Appl. No.: 12/524,136

(22) PCT Filed: Jan. 22, 2008

(86) PCT No.: PCT/US2008/051737
§ 371 (c)(1),
(2), (4) Date: Dec. 23, 2009

(87) PCT Pub. No.: WO2008/091913
PCT Pub. Date: Jul. 31, 2008

(65) Prior Publication Data
US 2010/0120035 A1   May 13, 2010

Related U.S. Application Data

(60) Provisional application No. 60/886,271, filed on Jan. 23, 2007.

(51) Int. Cl.
*C12Q 1/68* (2006.01)
*C12P 19/34* (2006.01)
(52) U.S. Cl. ...................... 435/6.12; 435/91.2
(58) Field of Classification Search .................... None
See application file for complete search history.

(56) References Cited

U.S. PATENT DOCUMENTS

| | | | |
|---|---|---|---|
| 5,786,146 | A | 7/1998 | Herman et al. |
| 6,884,586 | B2 | 4/2005 | Van Ness et al. |
| 7,112,404 | B2 | 9/2006 | Laird et al. |
| 2005/0009059 | A1 | 1/2005 | Shapero et al. |
| 2005/0019762 | A1 | 1/2005 | Olek |
| 2005/0064406 | A1 | 3/2005 | Zabarovsky et al. |
| 2005/0064428 | A1 | 3/2005 | Berlin |
| 2005/0069879 | A1 | 3/2005 | Berlin |
| 2005/0079521 | A1 | 4/2005 | Beaulieu et al. |
| 2005/0153316 | A1 | 7/2005 | Jeddeloh et al. |
| 2005/0153347 | A1 | 7/2005 | Shapero et al. |
| 2006/0210992 | A1 | 9/2006 | van den Boom et al. |

FOREIGN PATENT DOCUMENTS

| | | |
|---|---|---|
| WO | WO 02/086163 | 10/2002 |
| WO | WO 03/057909 | 7/2003 |
| WO | WO 03/080863 | 10/2003 |
| WO | WO 2004/013284 | 2/2004 |
| WO | WO 2005/012578 | 2/2005 |
| WO | WO 2005/040399 | 5/2005 |
| WO | WO 2008/091913 | 7/2008 |

OTHER PUBLICATIONS

Colella et al. *Biotechniques.* Jul. 2003;35(1):146-50;.
Costello et al., Aberrant CpG-island methylation has non-random and tumour-type-specific patterns, Nature (25) Feb. 2000 p. 132-138.
Dupont JM, Tost J, Jammes H, and Gut IG. *Anal Biochem*, Oct. 2004; 333(1): 119-27.
Eads et al., Cancer Res. 59:2302-2306, 1999.
Ehrich, M., et al. (Quantitative high-throughput analysis of DNA methylation patterns by base-specific cleavage and mass spectrometry. *Proc Natl Acad Sci* USA, 102, 15785-15790. (2005).
Frommer et al., Proc. Natl. Acad. Sci. USA 89:1827-1831, 1992.
Gonzalgo & Jones, Nucleic Acids Res. 25:2529-2531, 1997.
Grunau, C., et al. provide several different bisulfite treatment methods in "Bisulfite genomic sequencing: systematic investigation of critical experimental parameters" *Nucleic Acids Res*, 29, E65-65 (2001).
Hartmer, R., Storm, N., Boecker, S., Rodi, C.P., Hillenkamp, F., Jurinke, C. and van den Boom, D. (2003) RNase T1 mediated base-specific cleavage and MALDI-TOF MS for high-throughput comparative sequence analysis. *Nucleic Acids Res*, 31, e47.
Herman et al., Proc. Natl. Acad. Sci. USA 93:9821-9826, 1996.
International Preliminary Report on Patentability mailed Aug. 6, 2009, for International Application No. PCT/US08/51737 filed: Jan. 28, 2008.
International Search Report and Written Opinion mailed Aug. 8, 2008, for International Application No. PCT/US08/51737 filed: Jan. 28, 2008.
Laird, P.W. *Nature Reviews Cancer* 3, 253-266 (2003).
Olek, A., Oswald, J. and Walter, J. (1996) A modified and improved method for bisulphite based cytosine methylation analysis. *Nucleic Acids Res*, 24, 5064-5066.
Paulin, R., et al. (1998) Urea improves efficiency of bisulphite-mediated sequencing of 5'-methylcytosine in genomic DNA. *Nucleic Acids Res*, 26, 5009-5010.
Raizis, A.M., et al. (1995) a bisulfite method of 5-methylcytosine mapping that minimizes template degradation. *Anal Biochem*, 226, 161-166.
Sadri & Hornsby, Nucl. Acids Res. 24:5058-5059, 1996.
Tooke N and Pettersson M. *IVDT.* Nov. 2004; 41.
Toyota et al., Cancer Res. 59:2307-12, 1999.
Uhlmann, K. et al. *Electrophoresis* 23:4072-4079 (2002).
Vogelstein, B. and Kinzler, K.W. (1999) Digital PCR. *Proc Natl Acad Sci USA*, 96, 9236-9241).
Xiong & Laird, Nucleic Acids Res. 25:2532-2534, 1997.

*Primary Examiner* — Kenneth R. Horlick
*Assistant Examiner* — David Thomas
(74) *Attorney, Agent, or Firm* — Grant Anderson LLP

(57) ABSTRACT

The present invention is directed to methods useful for determining DNA quality after bisulfite treatment. The methods include a PCR-based assay, which allows ab-initio assessment of the DNA quality after bisulfite treatment and can help to prevent inaccurate quantitative measurement resulting from poor bisulfite treatment.

17 Claims, 9 Drawing Sheets

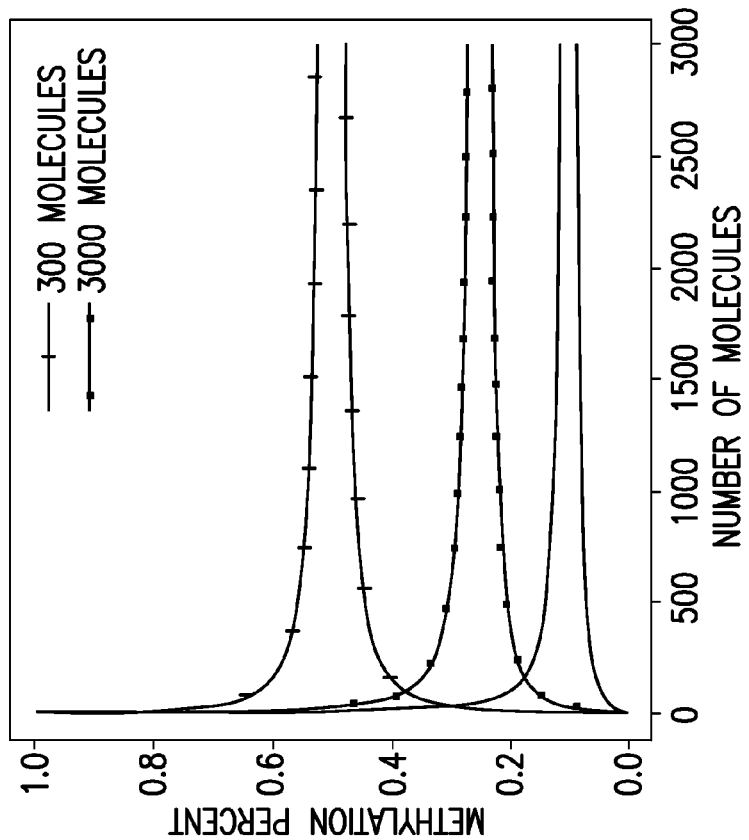
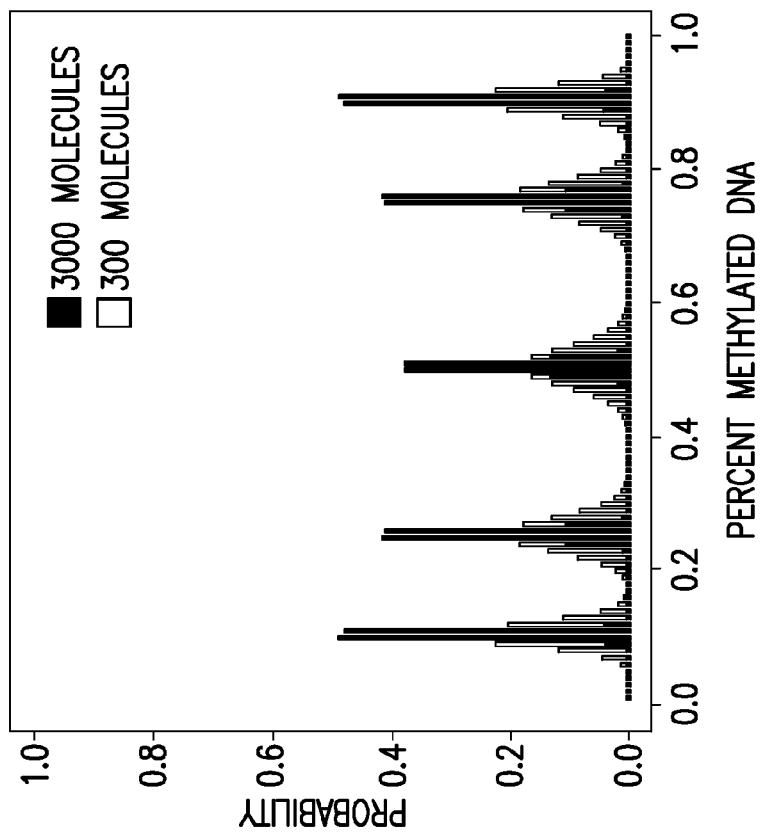
FIG.2B
FIG.2A

Primer Sequences

| Name | left primer | right primer |
|---|---|---|
| 176_M32053_01 | GTTGAGGGGTAGAGGGAAGTGT | ATCTTCAAACAAAAAAATAACC |
| 362_M32053_01 | GTTGAGGGGTAGAGGGAAGTGT | CTCACCAAAAACCAAAATAATAACC |
| 477_M32053_01 | TGTATATGGTTGGGGGTTAGTTG | CCCTCACCAAAAACCAAAATAATAAC |
| 617_M32053_01 | GGGTTGAGTATTGTTTTATTATTTTTTTTA | AACTACAAAACCCCAACAACCCT |
| 795_M32053_01 | GTTTTTTTTTAATTGGGGTGGTTT | CTCACCAAAAACCAAAATAATAACC |
| 960_M32053_01 | TTGTTAGATTTTAGATGTTTAAGGTGTTTT | CCTCACCAAAAACCAAAATAATAACC |

Genomic Sequences

176_M32053_01

GCTGAGGGGCAGAGGGAAGTGCCGCAAACCCCCTGGTGGGCGCGGTGCCAGCCCCCCAGGCCGATTCCCAT
CCAGTTGACCGAGCTTGTGCTGGTCACCGCGGTTTCCGCAGGACAGAGTCCCCACAGCCGCTGGGCACCCC
GGTCCCATTCGCGGCCACTTTCCTGTCTGAAGAC

362_M32053_01

GCTGAGGGGCAGAGGGAAGTGCCGCAAACCCCCTGGTGGGCGCGGTGCCAGCCCCCCAGGCCGATTCCCAT
CCAGTTGACCGAGCTTGTGCTGGTCACCGCGGTTTCCGCAGGACAGAGTCCCCACAGCCGCTGGGCACCCC
GGTCCCATTCGCGGCCACTTTCCTGTCTGAAGACCGCATGTTGCCGGGCTGTGCTTACGGCTCGCGGGCGC
ACTCTACTGACAAGCGGTGGGCGGCCTCACAGACTCTCCCAGGCCCGCGTGGGGCACCACGGTTGGGAGTG
GAGTGGAGACTGGCGAGTTTCGACTCCCCCAGCCACCCCGCTGTGGGTCCGTCGGTCACCACCTTGGCCTT
TGGTGAG

477_M32053_01

TGCACATGGCTGGGGGCCAGCTGCGGGTCCCTGGGGACTCGGATGGCACAGAGGGCCCCTTCCTGCCACCA
TCACGGCTCAGACCTCACGTTCCTGGAGAGTAGGGGTGGGGTGCTGAGGGGCAGAGGGAAGTGCCGCAAAC
CCCCTGGTGGGCGCGGTGCCAGCCCCCCAGGCCGATTCCCATCCAGTTGACCGAGCTTGTGCTGGTCACCG
CGGTTTCCGCAGGACAGAGTCCCCACAGCCGCTGGGCACCCCGGTCCCATTCGCGGCCACTTTCCTGTCTG
AAGACCGCATGTTGCCGGGCTGTGCTTACGGCTCGCGGGCGCACTCTACTGACAAGCGGTGGGCGGCCTCA
CAGACTCTCCCAGGCCCGCGTGGGGCACCACGGTTGGGAGTGGAGTGGAGACTGGCGAGTTTCGACTCCCC
CAGCCACCCCGCTGTGGGTCCGTCGGTCACCACCTTGGCCTTTGGTGAGGG

GGGCTGAGCATTGCCCCATCACCTCCCTCAGGGTCCAGGACTTCTCCCTCCCAGACCACTGTCTCCCCTCA
GGGGACACCATGCCTGCTGCTCCCTGCCTGCCAGCGCCCTGCACATACTTTGCACATGGCTGGGGGCCAGC
TGCGGGTCCCTGGGGACTCGGATGGCACAGAGGGCCCCTTCCTGCCACCATCACGGCTCAGACCTCACGTT
CCTGGAGAGTAGGGGTGGGGTGCTGAGGGGCAGAGGGAAGTGCCGCAAACCCCTGGTGGGCGCGGTGCCA
GCCCCCCAGGCCGATTCCCATCCAGTTGACCGAGCTTGTGCTGGTCACCGCGGTTTCCGCAGGACAGAGTC
CCCACAGCCGCTGGGCACCCCGGTCCCATTCGCGGCCACTTTCCTGTCTGAAGACCGCATGTTGCCGGGCT
GTGCTTACGGCTCGCGGGCGCACTCTACTGACAAGCGGTGGGCGGCCTCACAGACTCTCCCAGGCCCGCGT
GGGGCACCACGGTTGGGAGTGGAGTGGAGACTGGCGAGTTTCGACTCCCCCAGCCACCCCGCTGTGGGTCC
GTCGGTCACCACCTTGGCCTTTGGTGAGGGTTGTTGGGGCCCTGCAGTC

795_M32053_01

GCTTTTTCTAACTGGGGTGGCCCCGCCCAGAATTCCCGCCCCTGCCCTGCCGGCCAATCAGAGCAGGGCCC
TCCCGAGGGCCCCCGCAGGGCCCACCTCCGCCCTGGACAGTTCCAGCACACGTCTCTCTCACCCAGCACCC
ATCCTGGAATTCTCCAAAGACGGCCTCCCCGCACCCCTCCTTTGGCATCCGGAGACAGGGCTGAGCATTGC
CCCATCACCTCCCTCAGGGTCCAGGACTTCTCCCTCCCAGACCACTGTCTCCCCTCAGGGGACACCATGCC
TGCTGCTCCCTGCCTGCCAGCGCCCTGCACATACTTTGCACATGGCTGGGGGCCAGCTGCGGGTCCCTGGG
GACTCGGATGGCACAGAGGGCCCCTTCCTGCCACCATCACGGCTCAGACCTCACGTTCCTGGAGAGTAGGG
GTGGGGTGCTGAGGGGCAGAGGGAAGTGCCGCAAACCCCTGGTGGGCGCGGTGCCAGCCCCCCAGGCCGA
TTCCCATCCAGTTGACCGAGCTTGTGCTGGTCACCGCGGTTTCCGCAGGACAGAGTCCCCACAGCCGCTGG
GCACCCCGGTCCCATTCGCGGCCACTTTCCTGTCTGAAGACCGCATGTTGCCGGGCTGTGCTTACGGCTCG
CGGGCGCACTCTACTGACAAGCGGTGGGCGGCCTCACAGACTCTCCCAGGCCCGCGTGGGGCACCACGGTT
GGGAGTGGAGTGGAGACTGGCGAGTTTCGACTCCCCCAGCCACCCCGCTGTGGGTCCGTCGGTCACCACCT
TGGCCTTTGGTGAG

960_M32053_01

CTGCCAGACTCCAGATGTCCAAGGTGCTCCTTGGCTCCCACAAGCTCTCCTCCAGCACCCCATCTTCCCCT
GGTTGCCCCTCGGTTCCCCACTTCCCCAGTTTCCCCCGTTACCCCCCACCCATCCCACCCCCTCCCTCACC
CTGCTCCTCGGTCCTAGCCCGGGCTTTTTCTAACTGGGGTGGCCCCGCCCAGAATTCCCGCCCCTGCCCTG
CCGGCCAATCAGAGCAGGGCCCTCCCGAGGGCCCCCGCAGGGCCCACCTCCGCCCTGGACAGTTCCAGCAC
ACGTCTCTCTCACCCAGCACCCATCCTGGAATTCTCCAAAGACGGCCTCCCCGCACCCCTCCTTTGGCATC
CGGAGACAGGGCTGAGCATTGCCCCATCACCTCCCTCAGGGTCCAGGACTTCTCCCTCCCAGACCACTGTC
TCCCCTCAGGGGACACCATGCCTGCTGCTCCCTGCCTGCCAGCGCCCTGCACATACTTTGCACATGGCTGG
GGGCCAGCTGCGGGTCCCTGGGGACTCGGATGGCACAGAGGGCCCCTTCCTGCCACCATCACGGCTCAGAC
CTCACGTTCCTGGAGAGTAGGGGTGGGGTGCTGAGGGGCAGAGGGAAGTGCCGCAAACCCCTGGTGGGCG
CGGTGCCAGCCCCCCAGGCCGATTCCCATCCAGTTGACCGAGCTTGTGCTGGTCACCGCGGTTTCCGCAGG
ACAGAGTCCCCACAGCCGCTGGGCACCCCGGTCCCATTCGCGGCCACTTTCCTGTCTGAAGACCGCATGTT
GCCGGGCTGTGCTTACGGCTCGCGGGCGCACTCTACTGACAAGCGGTGGGCGGCCTCACAGACTCTCCCAG
GCCCGCGTGGGGCACCACGGTTGGGAGTGGAGTGGAGACTGGCGAGTTTCGACTCCCCCAGCCACCCCGCT
GTGGGTCCGTCGGTCACCACCTTGGCCTTTGGTGAGG

FIG.7B

METHOD FOR ACCURATE ASSESSMENT OF DNA QUALITY AFTER BISULFITE TREATMENT

RELATED PATENT APPLICATIONS

This patent application is a national stage of international patent application number PCT/US2008/051737, filed on Jan. 22, 2008, which claims the benefit of U.S. provisional patent application No. 60/886,271, filed on Jan. 23, 2007, entitled "Method for Accurate Assessment of DNA Quality after Bisulfite Treatment." The entire content of each of these patent applications hereby is incorporated by reference herein, including all text, drawings and tables, in jurisdictions providing for such incorporation.

SEQUENCE LISTING

The instant application contains a Sequence Listing which has been submitted via EFS-Web and is hereby incorporated by reference in its entirety. Said ASCII copy, created on Dec. 16, 2009, is named SEQ-6004-US.txt, and is 8,047 bytes in size.

FIELD OF USE

The invention pertains generally to nucleic acid assessment methods relating to quality of DNA after bisulfite treatment.

BACKGROUND

The covalent addition of methyl groups to cytosine has become an intensively researched epigenetic DNA marker. The vast majority of technologies used for DNA methylation analysis rely on a chemical reaction, the so-called "bisulfite-treatment", which introduces methylation-dependent sequence changes through selective chemical conversion of non-methylated Cytosine to Uracil. After treatment, all non-methylated Cytosine bases are converted to Uracil but all methylated Cytosine bases remain Cytosine. These methylation dependent C-to-U changes can subsequently be studied using conventional DNA analysis technologies.

SUMMARY

The bisulfite conversion protocol is susceptible to processing errors and small deviation from the protocol can result in failure of the treatment. Several attempts have been made to simplify the procedure and increase its robustness. Although significant achievements in this area have been made, bisulfite-treatment remains the main source of process variability in the analysis of DNA methylation. This variability in particular impairs assays, which strive for the quantitative assessment of DNA methylation. Thus, provided herein are methods useful for analyzing DNA methylation. The methods include a PCR-based assay, which allows ab-initio assessment of the DNA quality after bisulfite-treatment and can help to prevent inaccurate quantitative measurement resulting from poor bisulfite-treatment.

The invention in part provides a method to determine the maximum amplicon size for DNA in a sample after bisulfite treatment that will yield accurate quantitative measurements, comprising a) treating the sample with bisulfite; b) performing an amplification reaction using a primer set that amplifies at least 2 amplicons from a control region, wherein the amplicons increase in length in small increments and each amplicon is substantially covered by the next longer amplicon; c) analyzing at least 3 CpG sites that are common to all of the amplicons of step b) in regards to amplification success and statistical variability; and d) determining which of the amplicon sizes is suitable for the sample, wherein high amplification success and low statistical variability is indicative of an amplicon size that yields accurate quantitative measurements.

The invention also in part provides a method to determine the methylation conditions which yield results more accurate across a range of amplicon sizes for DNA in a sample, comprising: a) treating the sample with bisulfite; b) performing PCR using a primer set that amplifies at least two amplicons from a control region, wherein the amplicons increase in length in small increments and each amplicon is substantially covered by the next longer amplicon; c) modifying at least one of the methylation conditions to introduce variable methylation conditions; d) analyzing at least three CpG sites that are common to all of the amplicons of step b) with respect to amplification success and statistical variability; and e) determining which methylation conditions yield more accurate results across a range of amplicon sizes for DNA in a sample, wherein high amplification success and low statistical variability is indicative of methylation conditions that yield more accurate quantitative measurements. In one embodiment, the method is used to determine the optimal methylation conditions for one or more assays or for one or more samples. The methylation conditions may be selected from the group consisting of sample handling, bisulfite treatment methods, amplification conditions, and methylation detection methods. When determining the optimal amplification conditions, the amplification conditions may be selected from the group consisting of cycling temperatures, incubation time and PCR primer concentration.

In some embodiments, the bisulfite concentration of step a) is the same or substantially the same as the bisulfite concentration of a target assay. In certain embodiments, the amplification conditions of step b) are the same or substantially the same as the amplification conditions of a target assay. In some embodiments, the amplification reaction of step b) is a PCR reaction. In certain embodiments, the amplification reaction of step b) is done in a single reaction. In some embodiments, the amplification reaction of step b) amplifies at least 3, 4, 5 or 6 amplicons from a control region.

In certain embodiments, the primers of step b) bind to binding sites that are free of CpG sites. In some embodiments, the shortest amplicon is at least 100, 150 or 200 base pairs. In certain embodiments, the longest amplicon is no more than 900 base pairs. In some embodiments, the amplicons are increased in increments between about 100 and 150 base pairs. In certain embodiments, the amplicons cover substantially the same region.

In some embodiments, the control region comprises at least 3 CpG sites, and each CpG site has a known methylation ratio. In certain embodiments, the control region is the promoter region of IGF2/H19. In some embodiments, high amplification success is greater than 40% amplification success, greater than 50% amplification success, greater than 60% amplification success, greater than 70% amplification success, greater than 80% amplification success, greater than 90% amplification success or greater than 95% amplification success.

In certain embodiments, low statistical variability is less than 20%, 15%, 10%, 9%, 8%, 7%, 6%, 5%, 4%, 3%, 2% or 1%. In certain embodiments, the statistical variability is lower than the technical variability introduced by any of the methylation conditions.

The methods of the present invention may be particularly useful for samples with poor DNA quality (e.g., highly degraded), low amounts of DNA or high variability among different samples. In these cases, the present methods may be used to prioritize assays (e.g., only perform those assays that are confirmed to work based on amplicon size). In a related embodiment, the sample is a paraffin-embedded sample or any sample with poor quality and/or limited DNA.

The bisulfite treatment can be any bisulfite treatment known in the art, e.g., single standard bisulfite conversion protocol.

The methods of the present invention can be applied to any method that utilizes bisulfite treatment for nucleic acid analysis or any other nucleic acid treatment that leads to nucleic acid degradation. In a preferred embodiment, it is particularly useful for quantitative methylation analysis that is sensitive enough to detect differences less than 20%, 15%, 10%, 5%, 4%, 3%, 2% or 1%. In certain embodiments of the invention, the methods of the present invention may be used in conjunction with Sequenom's massCLEAVE™ technology, pyrosequencing, RT-PCR, Q-PCR, quantitative gene expression analysis or any known method for determining methylation state. In some embodiments, the methylation state is determined by multiplexed hME assays, fluorescence-based real-time PCR, methylation-sensitive single nucleotide primer extension, methylated CpG island amplification, methylation-specific PCR, restriction landmark genomic scanning, methylation-sensitive-representational difference analysis (MS-RDA), methylation-specific AP-PCR (MS-AP-PCR) methyl-CpG binding domain column/segregation of partly melted molecules (MBD/SPM), bisulfite sequencing direct, combined bisulfite restriction analysis (COBRA), PyroMeth™ technology or MethyLight™ technology.

BRIEF DESCRIPTION OF THE DRAWINGS

FIG. 2A and shows the probability distributions for observed methylation ratios based on the binomial distribution and different amounts of starting molecules. Shown are examples for 10, 25, 50 75 and 90% methylated molecules in the starting template. With a sample size of 3000 molecules, 95% of all randomly sampled probes will contain between 48 and 52% methylated DNA when the DNA sample contained 50% methylated DNA (darker colored distribution). However, when the DNA sample contains only 300 molecules this range is expanded from 43 to 57% (lighter colored distribution). FIG. 2B shows the 95% confidence intervals for sampling-means as a function of the number of the sampled molecules. Shown are results for 10% (upper curve), 25% (middle curve) and 50% (lower curve) methylated molecules in the starting template.

FIGS. 6C and 6D show results for 39 further PCR amplicons of different genomic regions ranging in length from 200 to 700 bp. FIG. 6C shows the percentage of successful quantitative measurements in relationship to the amplicon length. FIG. 6D shows a gel picture of the PCR results. Both confirm the results predicted from the use of the QC assay (FIGS. 6A and 6B).

FIG. 7 shows the primer sequences and the genomic sequences of the target regions for the assays described in Example 1. FIG. 7 discloses SEQ ID NOS 1-18, respectively, in order of appearance.

DEFINITIONS

Figure 1:
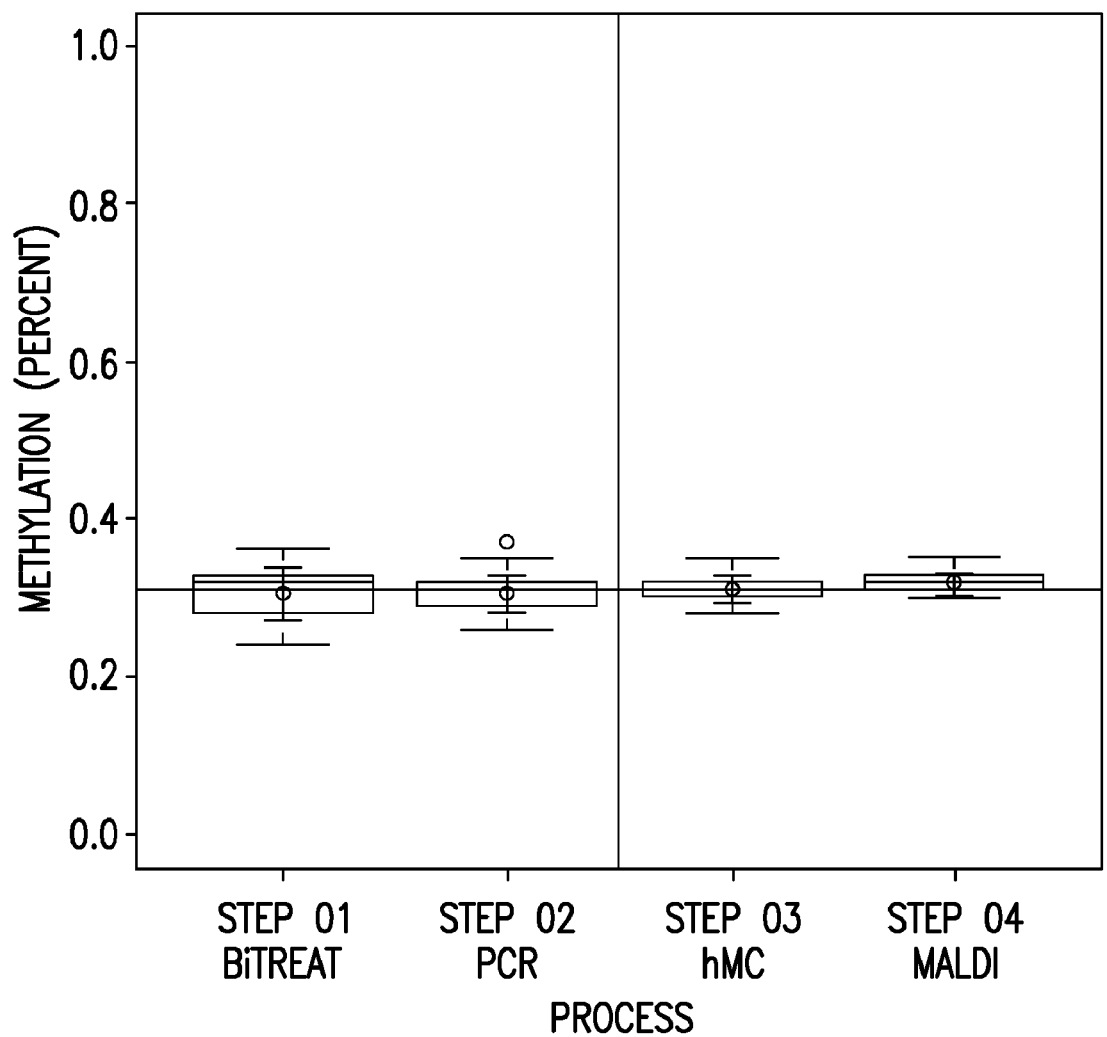
FIG. 1 shows a box plot graphic depicting the variability of repeated measurements for each step in the process (Step 1: bisulfite treatment; Step 2: PCR; Step 3: Sequenom's® Mass-CLEAVE; Step 4: MALDI-TOF MS analysis). Boxes are centered on the median and range from the lower to the upper quartile. Whiskers indicate the interquartile range. The small whiskers indicate the standard deviation from the mean. Bisulfite treatment and PCR can be identified as the greatest source of process variability. The post-PCR processing (MassCLEAVE™) and, in particular, the MALDI analysis show high precision in repeated measurements.

As used herein, a "sample" refers to a composition containing nucleic acid molecules to be detected, quantified or otherwise analyzed. Samples include "biological samples", which refer to any material obtained from a living or once-living source, for example, an animal such as a human or other mammal, a plant, a bacterium, a fungus, a protist or a virus or a processed form, such as amplified or isolated material. The biological sample can be in any form, including a solid material such as a tissue, cells, a cell pellet, a cell extract, a biopsy, tumor sample, lavage, or feces, or a biological fluid such as urine, whole blood, plasma, serum, interstitial fluid, peritoneal fluid, lymph fluid, ascites, sweat, saliva, follicular fluid, breast milk, non-milk breast secretions, cerebral spinal fluid, seminal fluid, lung sputum, amniotic fluid, exudate from a region of infection or inflammation, a mouth wash containing buccal cells, synovial fluid, or any other fluid sample produced by the subject. In addition, the sample can be solid samples of tissues or organs, such as collected tissues, including bone marrow, epithelium, stomach, prostate, kidney, bladder, breast, colon, lung, pancreas, endometrium, neuron, muscle, and other tissues. Samples can include organs, and pathological samples such as a formalin-fixed sample embedded in paraffin. If desired, solid materials can be mixed with a fluid or purified or amplified or otherwise treated. Samples examined using the methods described herein can be treated in one or more purification steps in order to increase the purity of the desired cells or nucleic acid in the sample. Samples also can be examined using the methods described herein without any purification steps to increase the purity of desired cells or nucleic acid.

As used herein, a "nucleic acid target region", or simply "target region", is a nucleic acid molecule that is examined using the methods disclosed herein. In a preferred embodiment, a target region is a fragment of genomic DNA or cDNA that contains one or more CpG sites.

As used herein, a "target assay" is a methylation-based assay directed to a target region. The methods of the present invention may be used to optimize and/or to perform quality control analysis for one or more target assays. In one embodiment, the target assay is a quantitative, high-throughput assay practiced in more than one location, for example, in various labs, hospitals or clinics, wherein it is important that the target assay is optimized to increase throughput and reduce cost while maintaining reproducibility and accuracy.

As used herein, a "CpG site" or "methylation site" refers to regions of DNA where a cytosine nucleotide occurs next to a guanine nucleotide in the linear sequence of bases along its length. Cytosines in CpG dinucleotides are capable of being methylated by DNA methyltransferases to form 5-methylcytosine. Regions of the DNA which have a higher concentration of CpG sites are known as CpG islands.

As used herein, a "methylation state" refers to the presence or absence of one or more methylated nucleotide bases or the ratio of methylated cytosine to unmethylated cytosine for a methylation site in a nucleic acid target region. Said ratio may also be referred to as "relative methylation". For example, a nucleic acid target region containing at least one methylated cytosine is considered methylated (i.e. the methylation state of the nucleic acid target region is methylated). A nucleic acid target region that does not contain any methylated nucleotides is considered unmethylated. Similarly, the methylation state of a nucleotide locus in a nucleic acid target region refers to the presence or absence of a methylated nucleotide at a particular locus in the nucleic acid target region. For example, the methylation state of a cytosine at the 7th nucleotide in a nucleic acid target region is methylated when the nucleotide present at the $7^{th}$ nucleotide in the nucleic acid target region is 5-methylcytosine. Similarly, the methylation state of a cytosine at the 7th nucleotide in a nucleic acid target region is unmethylated when the nucleotide present at the 7th nucleotide in the nucleic acid target region is cytosine (and not 5-methylcytosine). Correspondingly the ratio of methylated cytosine to unmethylated cytosine for a methylation site or sites can provide a methylation state of a nucleic acid target region.

As used herein, "methylation conditions" refer to the methods used to analyze the methylation state of one or more CpG sites, and the conditions under which said methods are practiced. As used herein, the analysis of a methylation state includes any pre- and post-analysis methods and conditions that may affect the outcome of said analysis. For example, methylation conditions may include, but are not limited to, sample handling, bisulfite treatment, amplification conditions and methylation detection methods. Methylation conditions may include a single condition or multiple conditions performed sequentially or in parallel.

As used herein, "sample handling" refers to how a sample is handled prior to methylation analysis. Sample handling includes, but is not limited to, how the sample is collected (e.g., blood draw, biopsy, etc.), the type of sample (tissue, bodily fluid, paraffin-embedded, etc.), the amount of sample, how the sample is stored (e.g., suspension method, container type, etc.), storage conditions (e.g., temperature, UV light presence, etc.), nucleic acid isolation or enrichment methods, and sample transfer methods (e.g., pipetting, robotic, etc.).

As used herein, "bisulfite treatment methods" refer to the methods and conditions (e.g., reagent concentrations) used to treat a sample with bisulfite, for example, for subsequent methylation analysis. As used herein, "treat", "treating" or grammatical variations thereof, refers to the process of exposing an analyte, typically a nucleic acid molecule, to conditions under which physical or chemical analyte modification or other chemical reactions (including enzymatic reactions) can occur. For example, as described herein, a nucleic acid target molecule may be treated with a reagent that modifies the nucleic acid target molecule as a function of its methylation state by adding a reagent such as bisulfite to a solution containing the nucleic acid target region. In treating the nucleic acid target with bisulfite, any unmethylated nucleotide, such as any unmethylated C nucleotide, present in the nucleic acid target molecule can be chemically modified, such as deaminated; however, if the nucleic acid target molecule contains no unmethylated selected nucleotide, such as no unmethylated C nucleotide, then a nucleic acid target molecule treated with such a reagent may not be chemically modified. Grunau, C., et al. provide several different bisulfite treatment methods in "Bisulfite genomic sequencing: systematic investigation of critical experimental parameters" *Nucleic Acids Res*, 29, E65-65 (2001).

As used herein, "amplification conditions" refer to the methods and conditions used to amplify nucleic acids. Amplification reactions include any means for multiplying the copies of a nucleic acid target region. Such methods include, but are not limited to, polymerase chain reaction (PCR), DNA ligase chain reaction (LCR), Q.beta.RNA replicase, and RNA transcription-based (TAS and 3SR) amplification reactions. Amplification conditions include, but are not limited to, cycling temperatures, cycling times, primer concentration, primer sequence and reaction reagents. In a preferred embodiment, amplification is done by PCR. Based on the 5' and 3' primers that are chosen, the region or regions of the nucleic acid molecule or nucleic acid molecules to be amplified may be selected. Amplification can be by any means known to those skilled in the art, including use of the PCR, transcription, and other such methods.

As used herein, "methylation detection methods" refer to the methods, conditions and instrumentation for analysis of DNA methylation. Examples of detection methods include, but are not limited to, multiplexed hME assays, fluorescence-based real-time PCR, methylation-sensitive single nucleotide primer extension, methylated CpG island amplification, methylation-specific PCR, restriction landmark genomic scanning, methylation-sensitive-representational difference analysis (MS-RDA), methylation-specific AP-PCR (MS-AP-PCR) methyl-CpG binding domain column/segregation of partly melted molecules (MBD/SPM), bisulphite sequencing direct, combined bisulfite restriction analysis (COBRA), PyroMeth™ technology or MethyLight™ technology. Examples of different instruments for the analysis of DNA methylation include, but are not limited to, mass spectrometers, nucleic acid sequencers (e.g., capillary sequencer), gel electrophoresis, fluorescence detectors (e.g., charge-coupled devices), thermal cyclers in conjunction with methylation-specific PCR, and HPLC. The methods of the present invention are particularly useful for nucleic acid-based quantitative analysis, for example, methylation analysis performed using Sequenom's® MassCLEAVE™

As used herein, an "amplicon" refers to the nucleic acid products resulting from the amplification of a target region. Amplification is often performed by PCR. Amplicons can range in size from 20 base pairs to 15000 base pairs in the case of long range PCR, but are more commonly 100-1000 base pairs for bisulfite-treated DNA used for methylation analysis. "Maximum amplicon size" refers to the maximum amplicon length that allows for high amplification success and low statistical variability.

As used herein, a "control region" refers to any genomic region (e.g., gene, promoter, UTR, intergenenic region, etc.) that contains at least 3 methylation sites. In a preferred embodiment, the methylation sites are highly methylated, e.g., the methylation percent at a given CpG site is greater than 40%. In certain embodiments, the control region is capable of binding to multiple PCR primers such that overlapping amplicons of incremental length are generated.

As used herein, a "primer set" refers to a collection of "oligonucleotide primers", or simply "primers" designed to amplify overlapping amplicons of incremental length. The primers of a primer set are polynucleotide sequences that hybridize to a sequence, preferably in a control region, and serve as a point of initiation of nucleic acid synthesis. A primer set usually consists of 2 or more forward and reverse primers that amplify multiple amplicons in the same genomic region. An example of a primer set is provided in FIG. 7, wherein the six forward and reverse primer pairs represent a primer set that may be used to amplify amplicons of the following lengths: 176 base pairs, 362 base pairs, 477 base pairs, 617 base pairs, 795 base pairs and 960 base pairs. Primers can be a variety of lengths and are often less than 50 nucleotides in length, for example 12-25 nucleotides, in length. The length and sequences of primers for use in PCR can be designed based on principles known to those of skill in the art.

As used herein, an "accurate quantitative measurement" refers to a precise measurement generated using the methods of the present invention, wherein the accurate quantitative measurement has a lower statistical variability than a measurement that is generated without using the methods of the present invention.

As used herein, "statistical variability" is a quantifiable variation of measurements of differing members of a population within the scale on which they are measured. A measure of statistical variability is a real number that is zero if all the data are identical, and increases as the data becomes more diverse. An important measure of dispersion is the standard deviation, which is the square root of the variance (which is itself a measure of dispersion). Other such measures include the range, the interquartile range, the mean difference, and the average absolute deviation.

As used herein, "amplification success" refers to the success rate of an amplification reaction. In the case of PCR, high amplification success results in the exponential amplification of a target region. Amplification success is a function of, inter alia, target region length and the occurrence of fragmentation.

High amplification success and low statistical variability is indicative of a suitable amplicon length or of optimal methylation conditions, which can be determined by one skilled in the art and may further depend on the intended use of the sample. For example, to achieve certain clinical standards, the statistical variability may have to be lower than those needed for research purposes.

DETAILED DESCRIPTION

Bisulfite Treatment

Several bisulfite treatment protocols are available, and most of them include mixing genomic DNA in a solution containing 6 molar urea and 2 molar sodium meta-bisulfite. The reaction is then incubated at pH 5.0 and 50° C. for 5 to 16 hours. This chemical treatment introduces various DNA strand breaks and results in highly fragmented single stranded DNA. Depurination has been identified as the main cause of DNA fragmentation during bisulfite treatment (Raizis, A. M., et al. (1995) A bisulfite method of 5-methylcytosine mapping that minimizes template degradation. *Anal Biochem*, 226, 161-166.). It has been shown that degradation of DNA affects between 84 to 96% of the DNA (Grunau, C., Clark, S. J. and Rosenthal, A. (2001) Bisulfite genomic sequencing: systematic investigation of critical experimental parameters. *Nucleic Acids Res*, 29, E65-65). Various attempts have been made to optimize bisulfite treatment by balancing competing goals of maintaining complete Cytosine conversion and minimal DNA fragmentation. (See, for example, Olek, A., Oswald, J. and Walter, J. (1996) A modified and improved method for bisulphite based cytosine methylation analysis. *Nucleic Acids Res*, 24, 5064-5066; and Paulin, R., et al. (1998) Urea improves efficiency of bisulphite-mediated sequencing of 5'-methylcytosine in genomic DNA. *Nucleic Acids Res*, 26, 5009-5010). Aggressive bisulfite treatment protocols (long incubation, high temperatures, high molarity of bisulfite) assure complete conversion of Cytosine to Uracil, but the genomic DNA can be degraded to a degree that renders PCR amplification impossible. Less aggressive treatments on the other hand carry the risk of overestimating methylation levels due to detection of nonconverted Cytosine.

PCR Amplification

High levels of DNA degradation decrease the number of DNA molecules, which are effectively available for PCR amplification. Therefore, PCR amplification strategies often rely on using large amounts of bisulfite treated DNA. Different amplification protocols recommend the use of 50 ng to 500 ng of bisulfite treated DNA. These strategies are not feasible for most research based on human samples, because DNA quantity usually is limited. In order to maximize the number of tests that can be run from one sample it is desirable to minimize the amount of DNA used per test. Recently, new assay formats and miniaturization has enabled routine amplification from as little as 10 ng bisulfite treated DNA. 10 ng of DNA equal approximately 6600 copies of genomic DNA. With more than 90% DNA degradation during bisulfite treatment only relatively few molecules are left for PCR amplification. The number of available molecules is also influenced by the length of the target amplicon. Longer amplicons are less likely to amplify, simply because the likelihood to find a single intact starting template decreases. This fact requires special attention if the analysis of DNA methylation is not restricted to a binary yes/no answer, but is required to provide quantitative results. When only few molecules are used as starting template statistical effects during the sampling procedure can have a dramatic effect on the quantitative result. Given this consideration it is apparent that a method for assessment of DNA quality in advance will dramatically help planning and interpreting quantitative methylation assays.

Quality Control Methods of the Invention

Current methods that allow a quality evaluation of bisulfite treated DNA are HPLC or gel-based assays. These assays require vast amounts of DNA and consume most of the product yielded by a single bisulfite conversion reaction. The present invention can be performed with as little as 30 ng of bisulfite treated DNA, and thus overcomes the relatively large amount of DNA needed for current methods.

The present invention is based on the fact that random DNA fragmentation reduces the number of available molecules for PCR amplification and subsequent methylation analysis, especially with increasing amplicon length. This random fragmentation has two main effects: one, when no intact DNA fragments are available for the targeted amplification region the PCR reaction will obviously fail; and two, when the number of available molecules is drastically reduced, to only a few available molecules due to DNA fragmentation, the results become similar to digital PCR (Vogelstein, B. and Kinzler, K. W. (1999) Digital PCR. *Proc Natl Acad Sci* USA, 96, 9236-9241). They are no longer quantitative and show large variability when measured repeatedly. The method presented here takes both of these effects into account.

The present invention comprises determining the amplification success and variance in the quantitative results from amplicons of increasing length for a genomic region with known methylation levels. The present invention enables improved measurement of quantitation variance, which requires high quantitation precision and low process variability. Methods for high throughput quantitative analysis of DNA methylation are described by Ehrich, M., et al. (Quantitative high-throughput analysis of DNA methylation patterns by base-specific cleavage and mass spectrometry. *Proc Natl Acad Sci* USA, 102, 15785-15790. (2005)) and in US Patent Application US20060210992, filed Jul. 9, 2004, which are hereby incorporated by reference. The method uses base-specific cleavage of single stranded nucleic acids coupled with MALDI-TOF MS detection. The assay allows quantitative analysis of all CpG sites within a given target region and is only limited in length by PCR success.

Methylation Detection Assays

The methylation status of a target nucleic acid may be determined using a number of different methods. In one aspect of the present invention, analysis of the DNA methylation of a nucleic acid target region is obtained by MALDI-TOF MS analysis of base-specific cleavage products derived from amplified nucleic acid target molecules. In general, a PCR amplification product is generated from bisulfite treated DNA, which is transcribed in vitro into a single stranded RNA molecule and subsequently cleaved base-specifically by an endoribonuclease. The conversion of cytosine to uracil during bisulfite treatment generates different base specific cleavage patterns that can be readily analyzed by MALDI-TOF MS. These spectral analyses may be used to determine the ratio of methylated versus non-methylated nucleotide at each methylation site of the nucleic acid target region. One skilled in the art will recognize that the methylation state of any nucleic acid, nucleic acid target region or gene of interest may be determined using the methods of the present invention. The methods of the present invention are particularly useful for quantitative methylation analysis.

Other methylation assay procedures are known in the art, and can be used in conjunction with the present invention. These assays allow for determination of the methylation state of one or a plurality of CpG islands within a DNA sequence. Such assays involve, among other techniques, DNA sequencing of bisulfite-treated DNA, PCR (for sequence-specific amplification), Southern blot analysis, use of methylation-sensitive restriction enzymes, etc.

For example, genomic sequencing has been simplified for analysis of DNA methylation patterns and 5-methylcytosine distribution by using bisulfite treatment (Frommer et al., Proc. Natl. Acad. Sci. USA 89:1827-1831, 1992). Additionally, restriction enzyme digestion of PCR products amplified from bisulfite-converted DNA is used, e.g., the method described by Sadri & Hornsby (Nucl. Acids Res. 24:5058-5059, 1996), or COBRA (Combined Bisulfite Restriction Analysis) (Xiong & Laird, Nucleic Acids Res. 25:2532-2534, 1997).

COBRA analysis is a quantitative methylation assay useful for determining DNA methylation levels at specific gene loci in small amounts of genomic DNA (Xiong & Laird, Nucleic Acids Res. 25:2532-2534, 1997). Briefly, restriction enzyme digestion is used to reveal methylation-dependent sequence differences in PCR products of sodium bisulfite-treated DNA. Methylation-dependent sequence differences are first introduced into the genomic DNA by standard bisulfite treatment according to the procedure described by Frommer et al. (Proc. Natl. Acad. Sci. USA 89:1827-1831, 1992). PCR amplification of the bisulfite converted DNA is then performed using primers specific for the interested CpG islands, followed by restriction endonuclease digestion, gel electrophoresis, and detection using specific, labeled hybridization probes. Methylation levels in the original DNA sample are represented by the relative amounts of digested and undigested PCR product in a linearly quantitative fashion across a wide spectrum of DNA methylation levels. In addition, this technique can be reliably applied to DNA obtained from microdissected paraffin-embedded tissue samples. Typical reagents (e.g., as might be found in a typical COBRA-based kit) for COBRA analysis may include, but are not limited to: PCR primers for specific gene (or methylation-altered DNA sequence or CpG island); restriction enzyme and appropriate buffer; gene-hybridization oligo; control hybridization oligo; kinase labeling kit for oligo probe; and radioactive nucleotides. Additionally, bisulfite conversion reagents may include: DNA denaturation buffer; sulfonation buffer; DNA recovery reagents or kits (e.g., precipitation, ultrafiltration, affinity column); desulfonation buffer; and DNA recovery components.

Preferably, assays such as "MethyLight™" (a fluorescence-based real-time PCR technique) (Eads et al., Cancer Res. 59:2302-2306, 1999), Ms-SNuPE (Methylation-sensitive Single Nucleotide Primer Extension) reactions (Gonzalgo & Jones, Nucleic Acids Res. 25:2529-2531, 1997), methylation-specific PCR ("MSP"; Herman et al., Proc. Natl. Acad. Sci. USA 93:9821-9826, 1996; U.S. Pat. No. 5,786,146), and methylated CpG island amplification ("MCA"; Toyota et al., Cancer Res. 59:2307-12, 1999) are used alone or in combination with other of these methods.

The MethyLight™ assay is a high-throughput quantitative methylation assay that utilizes fluorescence-based real-time PCR (TaqMan®) technology that requires no further manipulations after the PCR step (Eads et al., Cancer Res. 59:2302-2306, 1999). Briefly, the MethyLight™ process begins with a mixed sample of genomic DNA that is converted, in a sodium bisulfite reaction, to a mixed pool of methylation-dependent sequence differences according to standard procedures (the bisulfite process converts unmethylated cytosine residues to uracil). Fluorescence-based PCR is then performed either in an "unbiased" (with primers that do not overlap known CpG methylation sites) PCR reaction, or in a "biased" (with PCR primers that overlap known CpG dinucleotides) reaction. Sequence discrimination can occur either at the level of the amplification process or at the level of the fluorescence detection process, or both.

The MethyLight™ assay may be used as a quantitative test for methylation patterns in the genomic DNA sample, wherein sequence discrimination occurs at the level of probe hybridization. In this quantitative version, the PCR reaction provides for unbiased amplification in the presence of a fluorescent probe that overlaps a particular putative methylation site. An unbiased control for the amount of input DNA is provided by a reaction in which neither the primers, nor the probe overlie any CpG dinucleotides. Alternatively, a qualitative test for genomic methylation is achieved by probing of the biased PCR pool with either control oligonucleotides that do not "cover" known methylation sites (a fluorescence-based version of the "MSP" technique), or with oligonucleotides covering potential methylation sites.

The MethyLight™ process can by used with a "TaqMan®" probe in the amplification process. For example, double-stranded genomic DNA is treated with sodium bisulfite and subjected to one of two sets of PCR reactions using TaqMan® probes; e.g., with either biased primers and TaqMan® probe, or unbiased primers and TaqMan® probe. The TaqMan® probe is dual-labeled with fluorescent "reporter" and "quencher" molecules, and is designed to be specific for a relatively high GC content region so that it melts out at about 10° C. higher temperature in the PCR cycle than the forward or reverse primers. This allows the TaqMan® probe to remain fully hybridized during the PCR annealing/extension step. As the Taq polymerase enzymatically synthesizes a new strand during PCR, it will eventually reach the annealed TaqMan® probe. The Taq polymerase 5' to 3' endonuclease activity will then displace the TaqMan® probe by digesting it to release the fluorescent reporter molecule for quantitative detection of its now unquenched signal using a real-time fluorescent detection system.

Typical reagents (e.g., as might be found in a typical MethyLight™-based kit) for MethyLight™ analysis may include, but are not limited to: PCR primers for specific gene (or methylation-altered DNA sequence or CpG island); TaqMan® probes; optimized PCR buffers and deoxynucleotides; and Taq polymerase.

Ms-SNuPE. The Ms-SNuPE technique is a quantitative method for assessing methylation differences at specific CpG sites based on bisulfite treatment of DNA, followed by single-nucleotide primer extension (Gonzalgo & Jones, Nucleic Acids Res. 25:2529-2531, 1997).

Briefly, genomic DNA is reacted with sodium bisulfite to convert unmethylated cytosine to uracil while leaving 5-methylcytosine unchanged. Amplification of the desired target sequence is then performed using PCR primers specific for bisulfite-converted DNA, and the resulting product is isolated and used as a template for methylation analysis at the CpG site(s) of interest.

Small amounts of DNA can be analyzed (e.g., microdissected pathology sections), and it avoids utilization of restriction enzymes for determining the methylation status at CpG sites.

Typical reagents (e.g., as might be found in a typical Ms-SNuPE-based kit) for Ms-SNuPE analysis may include, but are not limited to: PCR primers for specific gene (or methylation-altered DNA sequence or CpG island); optimized PCR buffers and deoxynucleotides; gel extraction kit; positive control primers; Ms-SNuPE primers for specific gene; reaction buffer (for the Ms-SNuPE reaction); and radioactive nucleotides. Additionally, bisulfite conversion reagents may include: DNA denaturation buffer; sulfonation buffer; DNA recovery regents or kit (e.g., precipitation, ultrafiltration, affinity column); desulfonation buffer; and DNA recovery components.

MSP (methylation-specific PCR) allows for assessing the methylation status of virtually any group of CpG sites within a CpG island, independent of the use of methylation-sensitive restriction enzymes (Herman et al. Proc. Nat. Acad. Sci. USA 93:9821-9826, 1996; U.S. Pat. No. 5,786,146). Briefly, DNA is modified by sodium bisulfite converting all unmethylated, but not methylated cytosines to uracil, and subsequently amplified with primers specific for methylated versus unmethylated DNA. MSP requires only small quantities of DNA, is sensitive to 0.1% methylated alleles of a given CpG island locus, and can be performed on DNA extracted from paraffin-embedded samples. Typical reagents (e.g., as might be found in a typical MSP-based kit) for MSP analysis may include, but are not limited to: methylated and unmethylated PCR primers for specific gene (or methylation-altered DNA sequence or CpG island), optimized PCR buffers and deoxynucleotides, and specific probes.

The MCA technique is a method that can be used to screen for altered methylation patterns in genomic DNA, and to isolate specific sequences associated with these changes (Toyota et al., Cancer Res. 59:2307-12, 1999). Briefly, restriction enzymes with different sensitivities to cytosine methylation in their recognition sites are used to digest genomic DNAs from primary tumors, cell lines, and normal tissues prior to arbitrarily primed PCR amplification. Fragments that show differential methylation are cloned and sequenced after resolving the PCR products on high-resolution polyacrylamide gels. The cloned fragments are then used as probes for Southern analysis to confirm differential methylation of these regions. Typical reagents (e.g., as might be found in a typical MCA-based kit) for MCA analysis may include, but are not limited to: PCR primers for arbitrary priming Genomic DNA; PCR buffers and nucleotides, restriction enzymes and appropriate buffers; gene-hybridization oligos or probes; control hybridization oligos or probes.

Another method for analyzing methylation sites is a primer extension assay, including an optimized PCR amplification reaction that produces amplified targets for subsequent primer extension genotyping analysis using mass spectrometry. The assay can also be done in multiplex. This method (particularly as it relates to genotyping single nucleotide polymorphisms) is described in detail in PCT publication WO05012578A1 and US publication US20050079521A1. For methylation analysis, the assay can be adopted to detect bisulfite introduced methylation dependent C to T sequence changes. These methods are particularly useful for performing multiplexed amplification reactions and multiplexed primer extension reactions (e.g., multiplexed homogeneous primer mass extension (hME) assays) in a single well to further increase the throughput and reduce the cost per reaction for primer extension reactions.

Four additional methods for DNA methylation analysis include restriction landmark genomic scanning (RLGS, Costello et al., 2000), methylation-sensitive-representational difference analysis (MS-RDA), methylation-specific AP-PCR (MS-AP-PCR) and methyl-CpG binding domain column/segregation of partly melted molecules (MBD/SPM).

Additional methylation analysis methods that may be used in conjunction with the present invention are described in the following papers: Laird, P. W. *Nature Reviews Cancer* 3, 253-266 (2003); Biotechniques; Uhlmann, K. et al. *Electrophoresis* 23:4072-4079 (2002)-PyroMeth; Colella et al. *Biotechniques*. 2003 July; 35(1):146-50; Dupont J M, Tost J, Jammes H, and Gut I G. *Anal Biochem*, October 2004; 333 (1): 119-27; Tooke N and Pettersson M. *IVDT*. November 2004; 41; and the following published patents and patent applications: WO03080863A1, WO03057909A2, US2005/0153347, US20050009059A1, US20050069879A1, US20050064428A1, US20050064406A1, WO02086163C1, US20050019762A1, U.S. Pat. No. 6,884,586, WO04013284A2, US20050153316A1 and WO05040399A2.

EXAMPLES

Example 1

Assessment of DNA Quality Following Bisulfite Treatment and its Application to Subsequent Quantitative Analysis Bisulfite Treatment Bisulfite treatment of genomic DNA was performed with a commercial kit from Zymo Research Corporation (Orange, Calif.) that combines bisulfite conversion and DNA clean up. The kit follows a protocol from Paulin et al. (*Nucleic Acids Res*, 26, 5009-5010 (1998)). Briefly, in this protocol 2 µg of genomic DNA was denatured by the addition of 3 M sodium hydroxide and incubated for 15 min at 37° C. A 6.24 M urea/2 M sodium metabisulfite (4 M bisulfite) solution was prepared and added with 10 mM hydroquinone to the denatured DNA. The corresponding final concentrations were 5.36 M, 3.44 M and 0.5 mM respectively. This reaction mix was repeatedly heated between 55° C. for 15 min and 95° C. for 30 seconds in a PCR machine (MJ Tetrad™) for 20 cycles. Finally a DNA purification and cleaning step was performed.

Gel Based Fragmentation Analysis 2 ug of DNA was bisulfite treated using the EZ DNA Methylation Kit™ (Zymo Research Corporation, Orange, Calif.) and eluted in 10 µL water. 10 µL of the bisulfite treated DNA was loaded along with 5 µL of loading dye on a 4-8% TBE PAGE pre-cast gel (Jule, Inc, Milford, Conn.). 10 uL of 100 by ladder (Roche Applied Science, Indianapolis, Ind.) was loaded along side the DNA samples. Electrophoresis was performed using Novex Mini-Cell™ (Invitrogen, Carlsbad, Calif.) at 170 volts for 50 min. Prior to fluorescence detection, the gel was stained using SYBR Gold Gel Stain™ (Invitrogen, Carlsbad, Calif.) for 30 min on an agitator. Fluorescence detection was performed using the TYPHOON 8600™(GE Healthcare, Piscataway, N.J.) and densitometry measurements were calculated using the supplied Image Quant Software™

PCR and in vitro Transcription

The target regions were amplified using the primer pairs provided in FIG. 7. The PCR reactions were carried out in a total volume of 5 µl using 1 pmol of each primer, 40 µM dNTP, 0.1 U Hot Star Tag™ DNA polymerase (Qiagen), 1.5 mM MgCl2 and buffer supplied with the enzyme (final concentration 1×). The reaction mix was preactivated for 15 min at 95° C. The reactions were amplified in 45 cycles of 95° C. for 20 s, 62° C. for 30 s and 72° C. for 30 s followed by 72° C. for 3 min. Unincorporated dNTPs were dephosphorylated by adding 1.7ul $H_2O$ and 0.3 U Shrimp Alkaline Phosphatase (SEQUENOM, San Diego). The reaction was incubated at 37° C. for 20 min and SAP was then heat-inactivated for 10 minutes at 85° C. Typically, 2 microliters of the PCR reaction were directly used as template in a 6.5 µl transcription reaction. Twenty units of T7 R&DNA™ polymerase (Epicentre, Madison, Wis.) were used to incorporate either dCTP or dTTP in the transcripts. Ribonucleotides were used at 1 mM and the dNTP substrate at 2.5 mM; other components in the reaction were as recommended by the supplier. In the same step, the in vitro transcription RNase A (SEQUENOM, San Diego) was added to cleave the in vitro transcript. The mixture was then further diluted with $H_2O$ to a final volume of 27 µl. Conditioning of the phosphate backbone prior to MALDI-TOF MS was achieved by the addition of 6 mg CLEAN Resin™ (SEQUENOM Inc., San Diego, Calif.). Further experimental details are described elsewhere (Hartmer, R., Storm, N., Boecker, S., Rodi, C. P., Hillenkamp, F., Jurinke, C. and van den Boom, D. (2003) RNase T1 mediated base-specific cleavage and MALDI-TOF MS for high-throughput comparative sequence analysis. *Nucleic Acids Res*, 31, e47, which is hereby incorporated by reference).

Mass Spectrometry Measurements

Fifteen nl of the cleavage reactions were robotically dispensed onto silicon chips preloaded with matrix (SpectroCHIP™; SEQUENOM Inc., San Diego, Calif.). Mass spectra were collected using a MassARRAY™ mass spectrometer (Bruker-SEQUENOM). Spectra were analyzed using proprietary peak picking and spectra interpretation tools.

Statistical Analysis

All statistical simulations and calculations were carried out using the 'R' software package for statistical computing (Team, R.D.C. (2003) R: A language and environment for statistical computing). For the calculation of 95% confidence intervals of the binomial distribution, the 'binconf' function was used, which is part of the Hmisc package.

Results

The methods provided herein take into consideration the fragmentation pattern of bisulfite treated DNA, and the relationship between available template molecules and variation of methylation ratios caused by sampling error. Based on these considerations, the quality control assay described herein can be used to predict DNA quality and verify its applicability for subsequent experiments.

In this study all calculations are based on the DNA amounts used in the amplification protocol described herein. One µg of genomic DNA was used for bisulfite treatment. The treated DNA was eluted in 100 µl $H_2O$. One µl of this elution was used in each PCR reaction. This amount roughly equals 6000 DNA copies (10 ng DNA equals approximately 6600 DNA copies) and denotes the maximum number of molecules available for amplification assuming that no DNA degradation occurs. Unfortunately, DNA degradation is likely to occur and hence the number of available molecules can range between zero (complete degradation) and ~6000 (no degradation).

Stability of the Method

A prerequisite for the reliable measurement of the variance of quantitative methylation analysis is a stable method of detection that does not introduce any variability itself. To evaluate the variability of the detection method, the entire process was dissected into four steps and analyzed for process-specific variability at each step. One DNA was used in 16 replicated bisulfite treatments. Then an aliquot of each bisulfite treatment was pooled together and used for 16 individual PCR reactions. Again an aliquot from those PCR reactions was pooled and used for 16 individual base specific cleavage reactions. Finally, aliquots of the cleavage reactions were pooled and dispensed on 16 elements of a miniaturized array of matrix spots. FIG. 1 illustrates the process specific variability in a box plot. The results for each of the four tested conditions are summarized in an individual box plot. The analysis of all steps showed that process variability of the base specific cleavage reaction and the instrument measurements are minimal compared to the variability introduced by the PCR step and bisulfite treatment step (FIG. 1).

Simulation

To evaluate theoretical limitations of quantitative methylation analysis, the following assumptions were applied to the model system: Let N be the number of DNA molecules available for PCR amplification in the reaction. Suppose they have been drawn randomly and independently from the whole population of DNA molecules. Let p be the proportion of molecules in the whole population which are methylated. The number of methylated molecules in the reaction is a random variable X which follows a binomial distribution with parameters N and p. If Np and N(1-p) are both large enough, then X is approximately normally distributed with expected value Np and variance Np(1-p) with the appropriate continuity correction. Consequently the probability of observing a methylation ratio in an interval is the cumulative probability from the lower limit to the upper limit.

FIG. 2A shows the cumulative probability for two scenarios at 1% intervals. The highest bars are based on the assumption that 3000 molecules (50% degradation) are available for amplification. The shortest bars are calculations for 300 available molecules (95% degradation). Five scenarios of different methylation ratios in the starting template were calculated between 10 and 90% (10, 25, 50, 75 and 90%). As expected the probability distribution maximizes around the population mean. It was also determined which range most (95%) of the values for each methylation ratio are located. The graph reveals that for 50% methylation most values are located between 48 and 52% when staring with 6000 molecules. The range is dramatically larger with only 300 molecules and ranges from 43 to 57% methylation. To evaluate the relationship between methylation range and number of available DNA molecules, the 95% confidence interval for the binomial distribution was calculated as a function of available fragments for three different scenarios (10, 25 and 50% methylation) (FIG. 2B). The figure illustrates the strong correlation with the number of available fragments and indicates the dramatically increasing range of methylation ratios when the number of available fragments falls below 100-200.

Gel-Based Assessment of DNA Fragmentation

Figure 3:
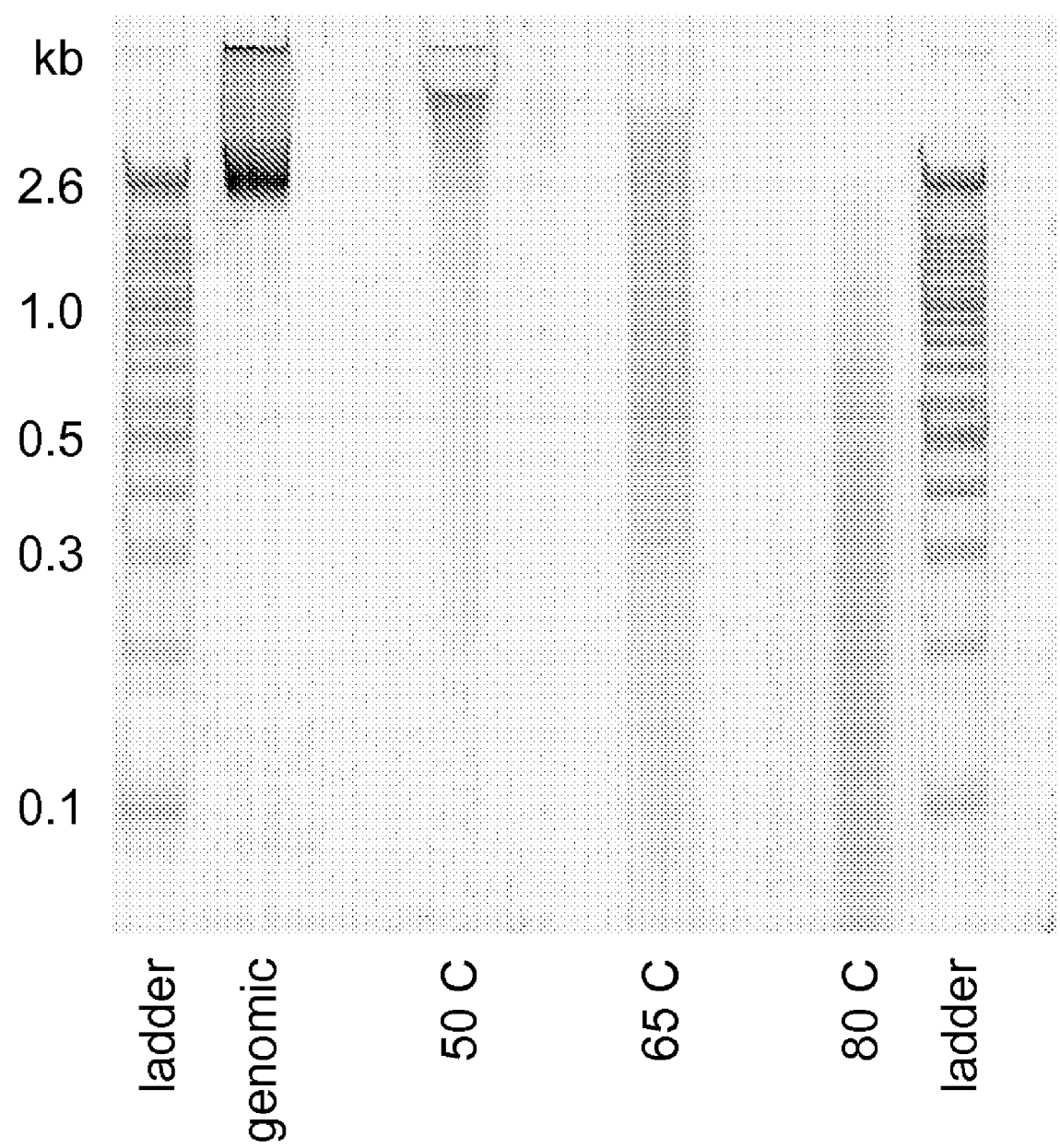
FIG. 3 is a gradient PAGE gel with CYBR Gold™ staining showing the DNA fragmentation of untreated genomic DNA (left) and after bisulfite treatment at varying temperatures (from left to right: 50° C., 65° C., 80° C.). The figure indicates that an increase of the incubation temperature during bisulfite treatment results in increased DNA fragmentation.

A densitometry-based analysis of original genomic DNA and DNA treated with three different bisulfite conversion protocols (A—incubation at 50° C.; B—incubation at 65° C.; C—incubation at 80° C. for 16 h) was performed to estimate the level of DNA fragmentation. To achieve the necessary sensitivity, 2 µg of bisulfite treated DNA was used on a 4 to 8% gradient PAGE gel, and stained with SYBR GOLD™ (FIG. 3). A densitometry calculation for the DNA size intervals of 100 bp was also performed. The interval for fragments below 100 bp could not be calculated accurately, because fragments below 75 bp are lost during the DNA cleanup.

For each of the four conditions, 2 µg of DNA were transferred onto the gel. The fragmented portions of the genomic DNA appear as a high intensity band around 2600 bp, while the high molecular weight genomic DNA is unable to enter the gel.

During bisulfite treatment, the genomic DNA is degraded, which results in a loss of the high intensity band at 2600 by and additional fragmentation of the previously unfragmented DNA. Consequently the signal intensities are distributed over a larger area and no single high intensity band is observed. The three different bisulfite protocols show varying fragment sizes. The resulting distribution of signal intensities is variable depending on the degradation levels. The largest fraction of DNA fragments is found to be >1500 by in length for condition A and around 200 by in length for condition C. These results confirm that higher incubation temperatures introduce higher levels of DNA fragmentation.

With depurination being the most likely cause for DNA fragmentation, the position of strand breaks can be assumed to be random. Thus higher DNA fragmentation is more likely to disrupt the desired amplification region and hence eliminate its availability for PCR amplification. This also has implications for the targeted amplicon length. When long amplicons are desired it, is more likely that a strand break will occur in-between the primer binding sites and consequently less molecules are available for amplification. Shorter target regions are less likely to have strand breaks and therefore are more likely to be successfully amplified. Hence, short amplicons and low fragmentation increase the probability of amplification success.

Consequently, an assay that utilizes amplicons of different length to estimate DNA fragmentation levels will be especially useful. In particular, a more accurate result can be given when employing a quantitative assay, because it can utilize information about measurement variance, rather than being limited to a binary yes/no answer.

QC Assay

To evaluate the feasibility of variable length amplicons to predict quality of bisulfite treated DNA, the IGF2/H19 region was used as the amplification target. Amplicon design should ideally cover the region with multiple amplicons increasing in length by small increments. Unfortunately, flexibility in primer design is constrained by genomic DNA features. The primer binding sites have to be free of any CpG sites and each amplicon should be almost entirely covered by the next longer amplicon. Also identical hybridization behavior of the different primer sets was implemented to enable simultaneous amplification in a single microtiter plate. For the IGF2 region, six amplicons were designed, which were 176, 362, 477, 617, 795, and 960 by in length (FIG. 4A). This set of six assays are hereafter referred to as control assays.

All amplicons were tested in 16 repeats on DNA treated with a single standard bisulfite conversion protocol. Consistent amplification was obtained for 176, 362, 477, 617, and sporadic amplification for 765. The longest amplicon failed to give any amplification results. This can be attributed to either bad primer design or to the fact that the bisulfite treated DNA does not provide enough intact copies for PCR amplification. Consequently, the first four amplicons (176, 362, 477 and 617 bp) became the focus for the quality control assay.

Figure 4B:
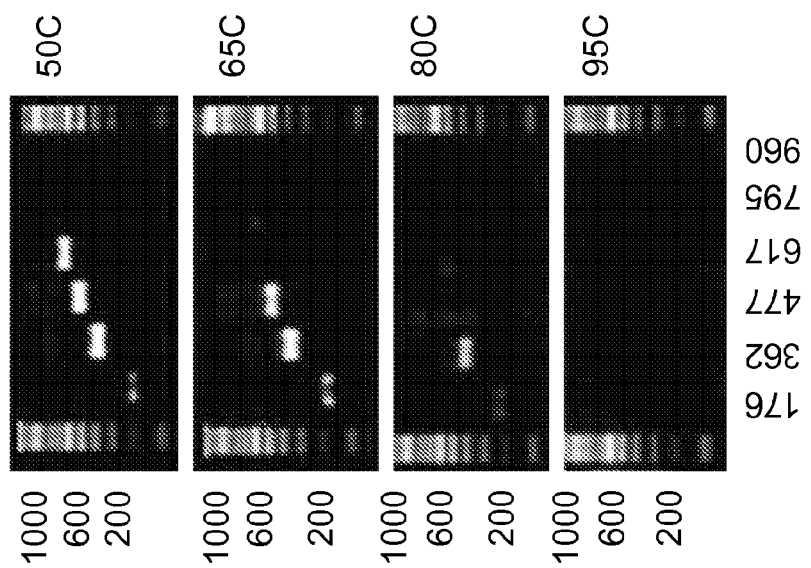
FIG. 4B shows an agarose gel for the six amplification products of the IGF2 region. Shown are PCR results for the six amplicons shown in FIG. 4A for four different bisulfite treatment incubation temperatures. The gel picture confirms that increasing incubation temperatures during bisulfite treatment lead to a decrease in the obtainable amplification length.
Figure 4A:
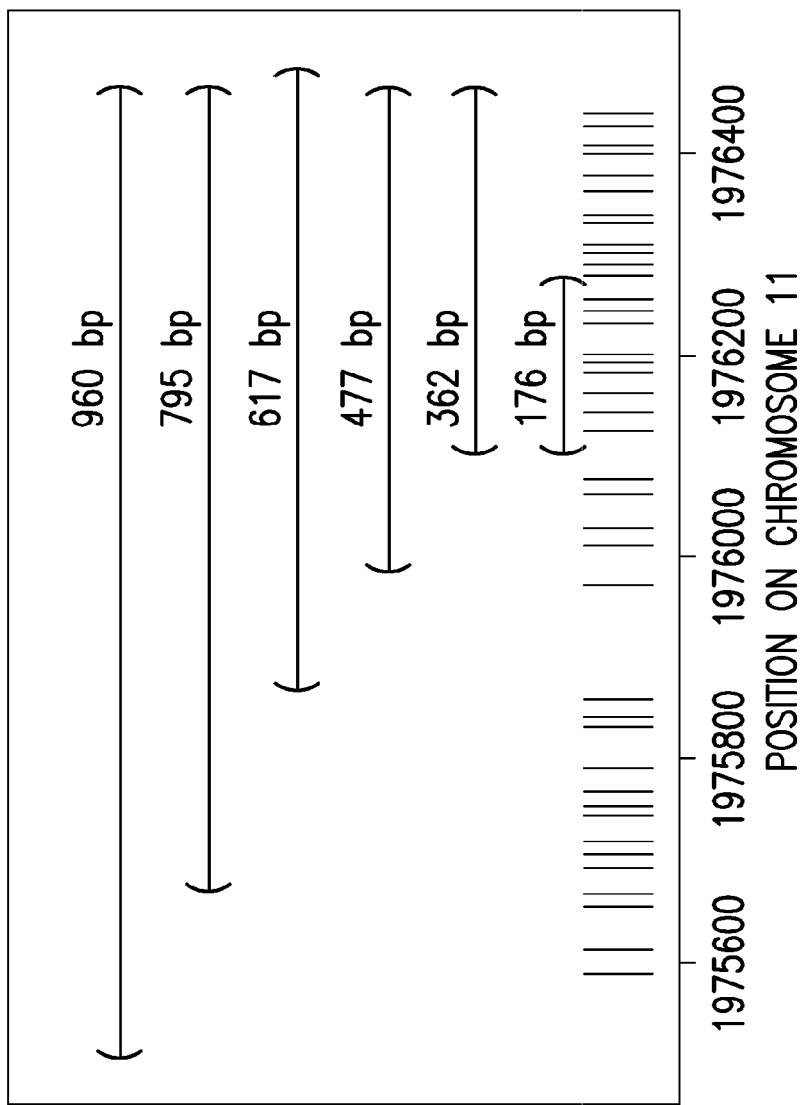
FIG. 4A shows a schematic representation of the different PCR amplicons and their genomic context on chromosome 11. All PCR amplicons share a subset of CpG sites (indicated as vertical stripes at the bottom of the Figure), which were used for comparison of methylation ratios.
Figure 5A:
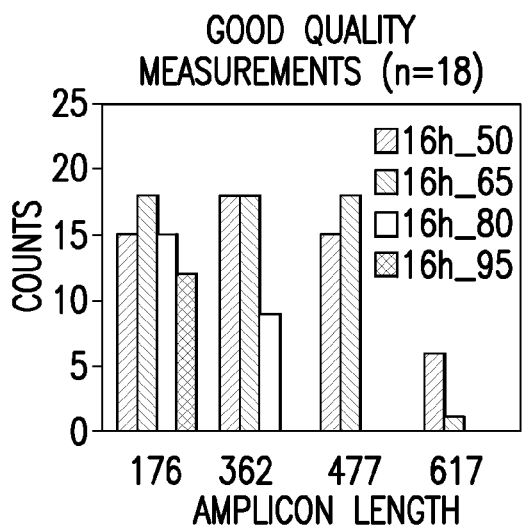
FIG. 5 contains bar graphs showing the number of high quality mass spectra for each amplicon length (two panels on the left). The panels on the right side show the corresponding standard deviations of the quantitative measurements. The bar graphs show results for different bisulfite incubation protocols. The results from 16 h incubation at constant temperature are shown in the upper two panels and results from a cycled incubation protocol are shown in the lower two panels. A total of 18 reactions were performed for each amplicon. Cycled incubation and lower incubation temperatures result in higher amplification success for longer amplicons and lower standard deviations on the determination of methylation ratios.
Figure 5B:
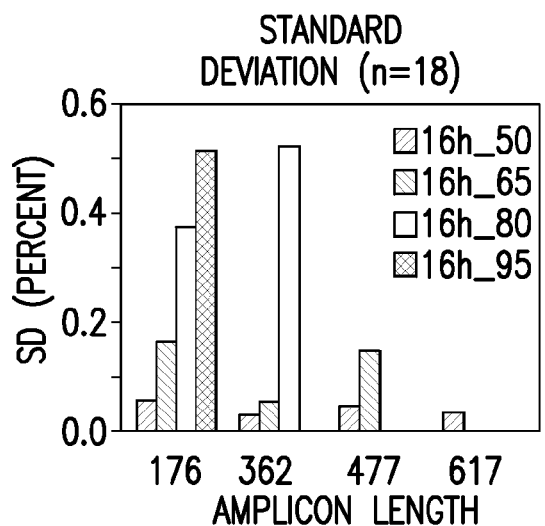
Figure 5C:
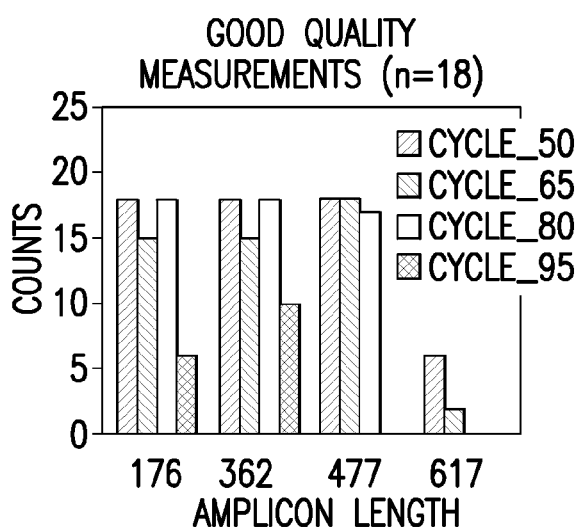
Figure 5D:
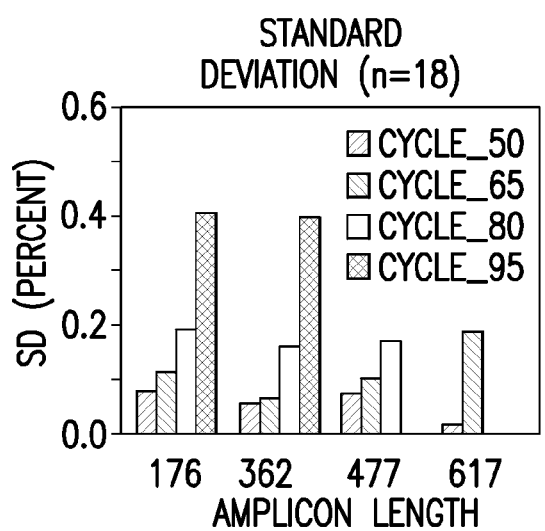

As a next step, increased fragmentation of DNA was induced by increasing incubation temperatures (50° C., 65° C., 80° C., 95° C.) during bisulfite treatment (FIG. 4B). The quality control assay was used to evaluate its ability to asses DNA quality. For each condition, bisulfite treatment was done in triplicate, and from each bisulfite treated DNA, duplicate PCR reactions were performed. To compare the quantitative results, three CpG sites were selected which were enclosed in all amplicons. The generated mass spectra were analyzed in regards to spectrum quality (wherein a spectrum of high quality has a high signal to noise ratio) and relative methylation (or methylation ratio) for the selected three CpG sites. In this setup, 18 quantitative measurements were obtained for each condition. The number of good quality measurements were summed as a first marker for amplification success. Mean methylation levels and standard deviation were also determined as a marker for sample bias.

The results show that incubation at 50° C. and 65° C. for 16 h yielded comparable results. Both show complete, good quality measurements up to an amplicon length of 477 bp and a decrease in good quality measurements for the 617 by amplicon. Standard deviation of repeated measurements in both cases is around 5% and therefore within instrument limitation. Incubation at 80° C. shows reduced quality beginning at 362 by and incubation at 95° C. results in less than 50% good quality at 176 bp. For 80° C. and 95° C. the obtained standard deviation of methylation ratios are well above the expected 5% (from 40% to 45%). When the individual values are closely examined, methylation varies between 0 and 100% (FIG. 5). This behavior is predicted by the simulations for very low numbers of available molecules. In the extreme case, it may be that only one molecule is available for amplification. This one molecule is then either methylated or non-methylated and therefore results in large differences in observed methylation ratios. The incubation at 80° C. exemplifies why measuring variance provides valuable information above the sole success rates. In this case, 15 out of 18 measurements were of good quality—suggesting that DNA quality is sufficient for the analysis of DNA methylation. However, the quantitative analysis reveals an amplification behavior similar to digital PCR. The observed methylation ratios cannot be measured reproducibly and therefore show high variance.

In a next step, a second incubation protocol was evaluated. Instead of incubation for 16 hours at a constant temperature, the temperature was cycled between the incubation temperature and a brief 95° C. denaturation step. The protocol comprises 20 cycles of 15 min at incubation temperature and 30 sec 95° C. resulting in a total incubation time of 5½ hours (FIG. 5 panel (c) and (d)). The data was analyzed according to the scheme described above. Incubation at 50° C. and 65° C. resulted in stable measurements up to 477 bp amplicon length, which is comparable to constant 16 h incubation. For 80° C. cycled incubation amplicons of length 176 and 362 by were of acceptable quality in contrast to the first 80° C. protocol where large variance was observed even in the short amplicons.

Incomplete bisulfite conversion was not observed under any of the used bisulfite treatment incubation protocols.

The results show that cycled incubation can improve the quality of bisulfite treated DNA. The results further indicate that the quality control assays described herein serve as effective methods for determining DNA quality, which improves assay design and quantification analysis.

Extrapolation to Multiple Amplicons

In the next step, the Inventor evaluated if results from this limited region can be generalized to the remaining genomic regions. A total of 39 amplicons from different regions in the genome with varying amplification lengths from 200 to 650 by were tested. Having demonstrated the general feasibility of using increasing temperatures to create differentially fragmented DNA, three instead of four temperatures were used for the fragmentation of DNA (A—50° C. 16 h; B—70° C. 16 h; C—90° C. 16 h). Each bisulfite treatment was done in triplicate. Each sample was evaluated with the quality control assay and across all samples. Finally the results were correlated to evaluate their concordance. In order to compare different length amplicons with different number of measurable CpG site, the amplification success of each amplicon was analyzed by calculating the ratio of successful quantitative CpG measurements to all possible CpG measurements.

Figure 6B:
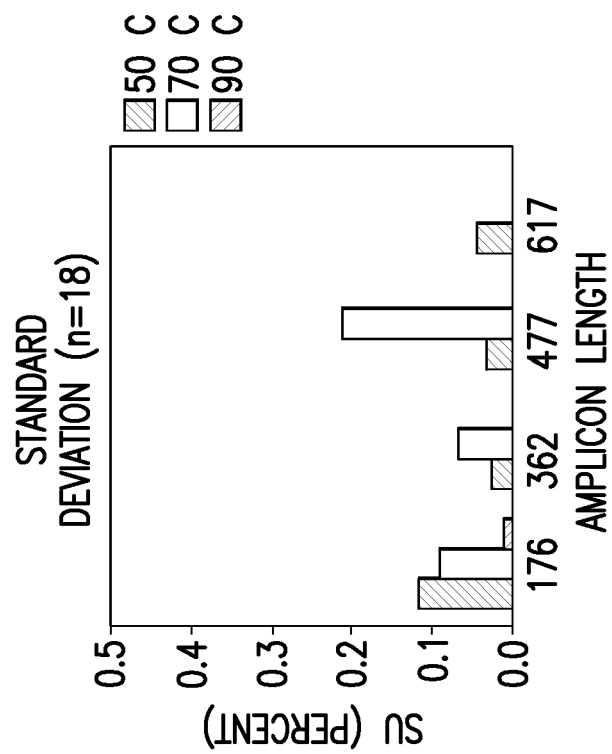
FIGS. 6A-D show the correlation between the results obtained from the quality control assays and PCR success from additional genomic targets of varying length. The bar graphs in FIGS. 6A and 6B show the results from the quality control assays similar to FIG. 5. The QC assay indicates that incubation at 90° C. limits amplification to only short amplicons (<300 bp), whereas incubation at 70° C. results in decreased amplification success for amplicons around 500 bp in length.
Figure 6A:
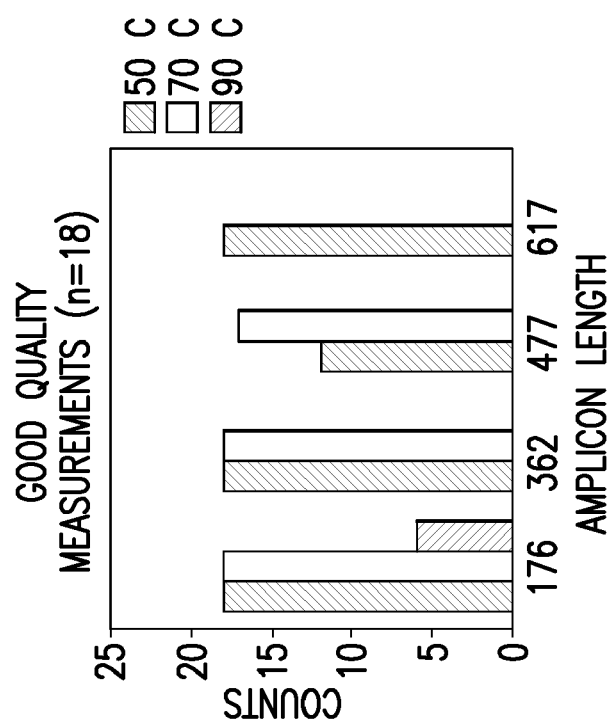

The quality control assay predicts good quality amplification up to 600 by for condition A. Condition B shows successful amplification at 477 bp, but with an increased methylation variance suggesting that this amplification length is borderline. For condition C, amplification success is dramatically reduced at 176 by suggesting impaired amplification of the shortest targets in the test set (FIGS. 6A and 6B).

Figure 6D:
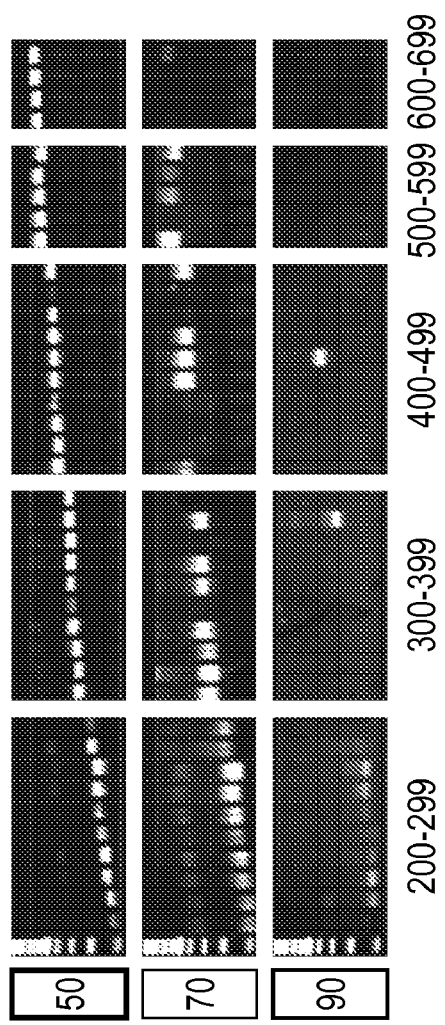
Figure 6C:
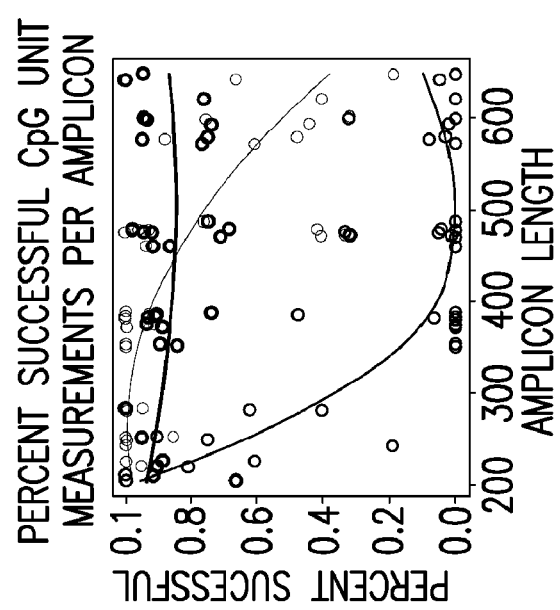

The results from the amplification of 39 selected target regions confirm the predictive power of the quality control assay. Condition A shows good amplification results throughout the entire range of amplicon lengths. For condition B, quality results start declining around 450 to 500 bp, and Condition C exhibits reduced quality from the shortest amplicons around 250 by (FIGS. 6C and 6D).

These results verify the ability of the presented quality control assay to predict the quality of bisulfite treated DNA and to estimate the chances for amplification success.

Assay Optimization

In another related Example, samples are spiked with a homogenous, non-human or otherwise distinguishable DNA source with a known methylation ratio such that methylation analysis methods can be optimized or quality controlled, for example, in different labs or clinical locations. The methods of the present invention may be practiced using the spiked samples so that an internal control is present during assay set-up and optimization, thus ensuring similar methods are practiced at all of the participating labs, hospitals or clinics. Similar results should be seen for all of the spiked samples.

The entirety of each patent, patent application, publication and document referenced herein hereby is incorporated by reference. Citation of the above patents, patent applications, publications and documents is not an admission that any of the foregoing is pertinent prior art, nor does it constitute any admission as to the contents or date of these publications or documents. Modifications may be made to the foregoing without departing from the basic aspects of the invention. Although the invention has been described in substantial detail with reference to one or more specific embodiments, those of ordinary skill in the art will recognize that changes may be made to the embodiments specifically disclosed in this application, yet these modifications and improvements are within the scope and spirit of the invention.

The invention illustratively described herein suitably may be practiced in the absence of any element(s) not specifically disclosed herein. Thus, for example, in each instance herein any of the terms "comprising," "consisting essentially of," and "consisting of" may be replaced with either of the other two terms. The terms and expressions which have been employed are used as terms of description and not of limitation, and use of such terms and expressions do not exclude any equivalents of the features shown and described or portions thereof, and various modifications are possible within the scope of the invention claimed. The term "a" or "an" can refer to one of or a plurality of the elements it modifies (e.g., "a primer" can mean one or more primers) unless it is contextually clear either one of the elements or more than one of the elements is described. The term "about" as used herein refers to a value sometimes within 10% of the underlying parameter (i.e., plus or minus 10%), a value sometimes within 5% of the underlying parameter (i.e., plus or minus 5%), a value sometimes within 2.5% of the underlying parameter (i.e., plus or minus 2.5%), or a value sometimes within 1% of the underlying parameter (i.e., plus or minus 1%), and sometimes refers to the parameter with no variation. For example, a length of "about 100 nucleotides" can include lengths between 90 nucleotides and 110 nucleotides. Thus, it should be understood that although the present invention has been specifically disclosed by representative embodiments and optional features, modification and variation of the concepts herein disclosed may be resorted to by those skilled in the art, and such modifications and variations are considered within the scope of this invention.

Embodiments of the invention are set forth in the claims which follow.

What is claimed is:

1. A method to determine the maximum amplicon size for DNA in a sample after bisulfite treatment that will yield accurate quantitative measurements, comprising:
   a) treating the sample with bisulfite;
   b) performing PCR using a primer set that amplifies at least two amplicons from a control region, wherein the amplicons increase in length in small increments and each amplicon is substantially covered by the next longer amplicon;
   c) analyzing at least three CpG sites that are common to all of the amplicons of step b) in regards to amplification success and statistical variability; and
   d) determining which of the amplicon sizes is suitable for a given sample, wherein high amplification success and low statistical variability is indicative of an amplicon size that yields accurate quantitative measurements.

2. A method to determine the optimal methylation conditions across a range of amplicon sizes for DNA in a sample, comprising:
   a) treating the sample with bisulfite;
   b) performing PCR using a primer set that amplifies at least two amplicons from a control region, wherein the amplicons increase in length in small increments and each amplicon is substantially covered by the next longer amplicon;
   c) modifying at least one of the methylation conditions to introduce variable methylation conditions;
   d) analyzing at least three CpG sites that are common to all of the amplicons of step b) in regards to amplification success and statistical variability; and
   e) determining which methylation conditions are optimal across a range of amplicon sizes for DNA in a sample, wherein high amplification success and low statistical variability is indicative of optimal methylation conditions that yield accurate quantitative measurements.

3. The method of claim 2, wherein the methylation conditions are selected from the group consisting of sample handling methods, bisulfite treatment methods, PCR conditions, methylation-related biochemistry methods and detection methods.

4. The method of claim 3, wherein the PCR conditions are selected from the group consisting of temperature, incubation time and PCR primer concentration.

5. The method of claim 1, wherein the bisulfite concentration of step a) is the same or substantially the same as the bisulfite concentration of a target assay.

6. The method of claim 1, wherein the PCR conditions of step b) are the same or substantially the same as the PCR conditions of a target assay.

7. The method of claim 1, wherein the primers of step b) bind to binding sites that are free of CpG sites.

8. The method of claim 1, wherein the PCR reaction of step b) is done in a single reaction.

9. The method of claim 1, wherein the PCR reaction of step b) amplifies at least 3 amplicons from a control region.

10. The method of claim 1, wherein the PCR reaction of step b) amplifies at least 4 amplicons from a control region.

11. The method of claim 1, wherein the shortest amplicon is at least 100 base pairs.

12. The method of claim 1, wherein the longest amplicon is no more than 900 base pairs.

13. The method of claim 1, wherein the amplicons are increased in increments between about 100 and 150 base pairs.

14. The method of claim 1, wherein the amplicons cover substantially the same region.

15. The method of claim 1, wherein the control region comprises at least 3 CpG sites, wherein each CpG site has a known methylation ratio.

16. The method of claim 1, wherein the control region is the promoter region of IGF2/H19.

17. A method to determine methylation conditions which yield results more accurate across a range of amplicon sizes for DNA in a sample, comprising:
   a) treating the sample with bisulfite;
   b) performing PCR using a primer set that amplifies at least two amplicons from a control region, wherein the amplicons increase in length in small increments and each amplicon is substantially covered by the next longer amplicon;
   c) modifying at least one of the methylation conditions to introduce variable methylation conditions;
   d) analyzing at least three CpG sites that are common to all of the amplicons of step b) in respect to amplification success and statistical variability; and
   e) determining which methylation conditions yield more accurate results across a range of amplicon sizes for DNA in a sample, wherein high amplification success and low statistical variability is indicative of methylation conditions that yield more accurate quantitative measurements;
   wherein the methylation conditions are selected from the group consisting of sample handling, bisulfite treatment methods, amplification conditions, and methylation detection methods.

* * * * *

SEQUENCE LISTING

<160> NUMBER OF SEQ ID NOS: 18

<210> SEQ ID NO 1
<211> LENGTH: 22
<212> TYPE: DNA
<213> ORGANISM: Artificial Sequence
<220> FEATURE:
<223> OTHER INFORMATION: Description of Artificial Sequence: Synthetic -continued primer

<400> SEQUENCE: 1
gttgaggggt agagggaagt gt                                          22

<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
atcttcaaac aaaaaaataa cc                                          22

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
gttgaggggt agagggaagt gt                                          22

<210> SEQ ID NO 4
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ctcaccaaaa accaaaataa taacc                                       25

<210> SEQ ID NO 5
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
tgtatatggt tgggggttag ttg                                         23

<210> SEQ ID NO 6
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
ccctcaccaa aaaccaaaat aataac                                      26

<210> SEQ ID NO 7
<211> LENGTH: 30
<212> TYPE: DNA
<213> ORGANISM: Artificial Sequence
<220> FEATURE:
<223> OTHER INFORMATION: Description of Artificial Sequence: Synthetic
      primer -continued

<400> SEQUENCE: 7
gggttgagta ttgttttatt attttttta                                    30

<210> SEQ ID NO 8
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
aactacaaaa ccccaacaac cct                                          23

<210> SEQ ID NO 9
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9 gttttttta attggggtgg ttt                                           23

<210> SEQ ID NO 10
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ctcaccaaaa accaaaataa taacc                                        25

<210> SEQ ID NO 11
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
ttgttagatt ttagatgttt aaggtgtttt                                   30

<210> SEQ ID NO 12
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
cctcaccaaa aaccaaaata ataacc                                       26

<210> SEQ ID NO 13
<211> LENGTH: 176
<212> TYPE: DNA
<213> ORGANISM: Homo sapiens

<400> SEQUENCE: 13
gctgaggggc agagggaagt gccgcaaacc ccctggtggg cgcggtgcca gccccccagg    60
ccgattccca tccagttgac cgagcttgtg ctggtcaccg cggtttccgc aggacagagt   120

```
cccacagcc gctgggcacc ccggtcccat tcgcggccac tttcctgtct gaagac      176
```

<210> SEQ ID NO 14
<211> LENGTH: 362
<212> TYPE: DNA
<213> ORGANISM: Homo sapiens

<400> SEQUENCE: 14

```
gctgaggggc agagggaagt gccgcaaacc ccctggtggg cgcggtgcca gccccccagg   60
ccgattccca tccagttgac cgagcttgtg ctggtcaccg cggtttccgc aggacagagt  120
ccccacagcc gctgggcacc ccggtcccat tcgcggccac tttcctgtct gaagaccgca  180
tgttgccggg ctgtgcttac ggctcgcggg cgcactctac tgacaagcgg tgggcggcct  240
cacagactct cccaggcccg cgtggggcac acgttggg agtggagtgg agactggcga   300
gtttcgactc ccccagccac cccgctgtgg gtccgtcggt caccaccttg gcctttggtg  360
ag                                                                 362
```

<210> SEQ ID NO 15
<211> LENGTH: 477
<212> TYPE: DNA
<213> ORGANISM: Homo sapiens

<400> SEQUENCE: 15

```
tgcacatggc tgggggccag ctgcgggtcc ctggggactc ggatggcaca gagggcccct   60
tcctgccacc atcacggctc agacctcacg ttcctggaga gtaggggtgg ggtgctgagg  120
ggcagaggga agtgccgcaa accccctggt gggcgcggtg ccagcccccc aggccgattc  180
ccatccagtt gaccgagctt gtgctggtca ccgcggtttc gcaggacag agtccccaca   240 gccgctgggc accccggtcc cattcgcggc cactttcctg tctgaagacc gcatgttgcc  300
gggctgtgct tacggctcgc gggcgcactc tactgacaag cggtgggcgg cctcacagac  360
tctcccaggc ccgcgtgggg caccacggtt gggagtggag tggagactgg cgagtttcga  420
ctcccccagc caccccgctg tgggtccgtc ggtcaccacc ttggcctttg gtgaggg     477
```

<210> SEQ ID NO 16
<211> LENGTH: 617
<212> TYPE: DNA
<213> ORGANISM: Homo sapiens

<400> SEQUENCE: 16

```
gggctgagca ttgccccatc acctccctca gggtccagga cttctccctc ccagaccact   60
gtctcccctc aggggacacc atgcctgctg ctccctgcct gccagcgccc tgcacatact  120
ttgcacatgg ctgggggcca gctgcgggtc cctggggact cggatggcac agagggcccc  180
ttcctgccac catcacggct cagacctcac gttcctggag agtaggggtg gggtgctgag  240
gggcagaggg aagtgccgca aaccccctgg tgggcgcggt gccagccccc aggccgatt  300 cccatccagt tgaccgagct tgtgctggtc accgcggttt cgcaggacag agtccccac   360 agccgctggg caccccggtc ccattcgcgg ccactttcct gtctgaagac cgcatgttgc  420
cgggctgtgc ttacggctcg cgggcgcact ctactgacaa gcggtgggcg gcctcacaga  480
ctctcccagg cccgcgtggg gcaccacggt tgggagtgga gtggagactg gcgagtttcg  540
actcccccag ccaccccgct gtgggtccgt cggtcaccac cttggccttt ggtgagggtt  600
gttggggccc tgcagtc                                                 617
```

<210> SEQ ID NO 17
<211> LENGTH: 795
<212> TYPE: DNA
<213> ORGANISM: Homo sapiens

<400> SEQUENCE: 17

```
gcttttcta actggggtgg ccccgcccag aattcccgcc cctgccctgc cggccaatca      60
gagcagggcc ctcccgaggg ccccgcagg gcccacctcc gccctggaca gttccagcac     120
acgtctctct cacccagcac ccatcctgga attctccaaa gacggcctcc ccgcacccct    180
cctttggcat ccggagacag ggctgagcat tgccccatca cctccctcag ggtccaggac    240
ttctccctcc cagaccactg tctcccctca ggggacacca tgcctgctgc tccctgcctg    300
ccagcgccct gcacatactt tgcacatggc tggggccag ctgcgggtcc ctggggactc    360
ggatggcaca gagggcccct tcctgccacc atcacggctc agacctcacg ttcctggaga    420
gtaggggtgg ggtgctgagg ggcagaggga agtgccgcaa accccctggt gggcgcggtg    480
ccagcccccc aggccgattc ccatccagtt gaccgagctt gtgctggtca ccgcggtttc    540
cgcaggacag agtccccaca gccgctgggc accccggtcc cattcgcggc cactttcctg    600
tctgaagacc gcatgttgcc gggctgtgct tacggctcgc gggcgcactc tactgacaag    660
cggtgggcgg cctcacagac tctcccaggc ccgcgtgggg caccacggtt gggagtggag    720
tggagactgg cgagtttcga ctcccccagc caccccgctg tgggtccgtc ggtcaccacc    780
ttggcctttg gtgag                                                     795
```

<210> SEQ ID NO 18
<211> LENGTH: 960
<212> TYPE: DNA
<213> ORGANISM: Homo sapiens

<400> SEQUENCE: 18

```
ctgccagact ccagatgtcc aaggtgctcc ttggctccca caagctctcc tccagcaccc     60
catcttcccc tggttgcccc tcggttcccc acttccccag tttcccccgt taccccccac    120
ccatcccacc ccctccctca ccctgctcct cggtcctagc ccgggcttt tctaactggg    180
gtggccccgc ccagaattcc cgccctgcc ctgccggcca atcagagcag ggccctcccg    240
agggcccccg cagggcccac ctccgccctg gacagttcca gcacacgtct ctctcaccca    300
gcacccatcc tggaattctc caaagacggc ctccccgcac cctcctttg gcatccggag    360
acagggctga gcattgcccc atcacctccc tcagggtcca ggactctctcc ctcccagacc    420
actgtctccc ctcaggggac accatgcctg ctgctccctg cctgccagcg ccctgcacat    480
actttgcaca tggctggggg ccagctgcgg gtccctgggg actcggatgg cacagagggc    540
cccttcctgc caccatcacg gctcagacct cacgttcctg gagagtaggg gtggggtgct    600
gaggggcaga gggaagtgcc gcaaaccccc tggtgggcgc ggtgccagcc cccaggccg    660
attcccatcc agttgaccga gcttgtgctg gtcaccgcgg tttccgcagg acagagtccc    720
cacagccgct gggcaccccg gtcccattcg cggccacttt cctgtctgaa gaccgcatgt    780
tgccgggctg tgcttacggc tcgcgggcgc actctactga caagcggtgg gcggcctcac    840
agactctccc caggcccgcg tggggcaccac ggttgggagt ggagtggaga ctggcgagtt    900
tcgactcccc cagccacccc gctgtgggtc cgtcggtcac caccttggcc tttggtgagg    960
```